United States Patent
Yu et al.

(10) Patent No.: US 9,006,535 B2
(45) Date of Patent: Apr. 14, 2015

(54) ABIOTIC STRESS TOLERANT TRANSGENIC PLANTS

(75) Inventors: Su-May Yu, Taipei (TW); Tuan-Hua David Ho, Taipei (TW)

(73) Assignee: Academia Sinica, Taipei (TW)

( * ) Notice: Subject to any disclaimer, the term of this patent is extended or adjusted under 35 U.S.C. 154(b) by 961 days.

(21) Appl. No.: 11/942,134

(22) Filed: Nov. 19, 2007

(65) Prior Publication Data

US 2009/0133154 A1  May 21, 2009

(51) Int. Cl.
*A01H 1/00* (2006.01)
*A01H 5/00* (2006.01)
*C12N 15/82* (2006.01)
*A23L 1/10* (2006.01)

(52) U.S. Cl.
CPC ............... *C12N 15/8237* (2013.01); *A23L 1/10* (2013.01); *C12N 15/8271* (2013.01); *C12N 15/8273* (2013.01)

(58) Field of Classification Search
None
See application file for complete search history.

(56) References Cited

U.S. PATENT DOCUMENTS 5,981,842 A    11/1999   Wu et al.
6,670,528 B1 * 12/2003   Shinozaki et al. ............ 800/298
6,951,971 B1   10/2005   Wu et al.

OTHER PUBLICATIONS

Shen et al. (The Plant Cell, 8:1107-1119, Jul. 1999).*
Xu et al. (Plant Physiol., 110:249-257, 1999).*
Hong et al. (Plant Molecular Biology, 11:495-506, 1988).*
Shen et al. (Plant Molecular Biology, 54:111-124, 2004).*
Su et al. (Plant Physiol., 117:913-922, 1998).*
Day et al. (Genes Dev. 14:2869-2880; 2000).*
Fu D, Huang B, Xiao Y, Muthukrishnan S, Liang G (2007), Overexpression of barley hva gene in creeping bentgrass for improving drought tolerance. Plant Cell Rep 26: 467-477.
Garg AK, Kim JK, Owens TG, Ranwala AP, Choi YD, Kochian LV, Wu RJ (2002), Trehalose accumulation in rice plants confers high tolerance levels to different abiotic stresses. Proc Natl Acad Sci U S A 99:15898-15903.
Hong B, Barg R, Ho T-H (1992), Developmental and organ-specific expression of an ABA- and stress-induced protein in barley. Plant Mol Biol 18: 663-674.
Hong B, Uknes S, Ho T-H (1988), Cloning and characterization of a cDNA encoding a mRNA rapidly induced by ABA in barley aleurone layers. Plant Mol Biol 11: 495-506.
Lee J, Prasad V, Yang P, Wu J, Ho T-H, Charng YY, Chan MT, (2003) Expression of *Arabidopsis* CBF1 regulated by an ABA/stress inducible promoter in transgenic tomato confers stress tolerance without affecting yield. Plant Cell Environ 26: 1181-1190.
Maqbool S, Zhong H, EI-Maghraby Y, Ahmad A, Chai B, Wang W, Sabzikar R, Sticklen M (2002), Competence of oat (*Avena sativa* L.) shoot apical meristems for integrative transformation, inherited expression, and osmotic tolerance of transgenic lines containing hva1. Theor Appl Genet 105: 201-208.
Shen Q, Ho TH (1995), Functional dissection of an abscisic acid (ABA)-inducible gene reveals two independent ABA-responsive complexes each containing a G-box and a novel cis-acting element. The Plant Cell 7: 295-307.
Shen Q, Zhang P, Ho TH (1996), Modular nature of abscisic acid (ABA) response complexes: composite promoter units that are necessary and sufficient for ABA induction of gene expression in barley. The Plant Cell 8:1107-1119.
Shen QJ, Casaretto JA, Zhang P, Ho TH (2004), Functional definition of ABA-response complexes: the promoter units necessary and sufficient for ABA induction of gene expression in barley (*Hordeum vulgare* L.). Plant Mol Biol 54: 111-124.
Sivamani E, Bahieldin A, Wraith JM, Al-Niemi T, Dyer WE, Ho TD, Qu R (2000), Improved biomass productivity and water use efficiency under water deficit conditions in transgenic wheat constitutively expressing the barley HVA1 gene. Plant Science 155:1-9.
Straub PF, Shen Q, Ho TD (1994) Structure and promoter analysis of an ABA-and stress-regulated barley gene, HVA1. Plant Mol Biol 26: 617-630.
Su J, Shen Q, David Ho TH, Wu R (1998) Dehydration-stress-regulated transgene expression in stably transformed rice plants. Plant Physiol 117: 913-922.
Sutton F, Ding X, Kenefick DG (1992), Group 3 LEA Gene HVA1 Regulation by Cold Acclimation and Deacclimation in Two Barley Cultivars with Varying Freeze Resistance. Plant Physiol 99: 338-340.
Xu D, Duan X, Wang B, Hong B, Ho T, Wu R (1996), Expression of a Late Embryogenesis Abundant Protein Gene, HVA1, from Barley Confers Tolerance to Water Deficit and Salt Stress in Transgenic Rice. Plant Physiol 110: 249-257.
Houde M, Belcaid M, Ouellet F, Danyluk J, Monroy A, Dryanova A, Gulick P, Bergeron A, Laroche A, Links M, MacCarthy L, Crosby W, Sarhan F, (2006), Wheat EST resources for functional genomics of abiotic stress, BMC Genomics 7:149, pp. 1-22.

* cited by examiner

*Primary Examiner* — Vinod Kumar

(74) *Attorney, Agent, or Firm* — Panitch Schwarze Belisario & Nadel LLP

(57) ABSTRACT

In a transgenic plant, a stress-responsive promoter containing CE3 and ABRE2 from HVA1 ABRC3 and CE1 from HVA22 ABRC1, directs low background expression of a gene under normal growth conditions, but is highly inducible by an abiotic stress, such as abscisic acid, dehydration, salt or cold. Compared with the wild type plant, the transgenic plant that expresses a stress-resistant gene under the control of the stress-responsive promoter is more resistant and/or tolerant to abiotic stresses and exhibits similar or higher growth rate and strength under regular or normal environmental conditions.

10 Claims, 12 Drawing Sheets

A ABRC321

```
                    ┌─── CE3 ───┬── A2 ──┐         ┌─ CE1 ─┐
SEQ ID NO:5   ggtaccGCAACGCGTGTCCTCCCTACGTGGCGGCtcgagATTGCCACCGGtctaga
SEQ ID NO:14  ccatggCGTTGCGCACAGGAGGGATGCACCGCCGagctcTAACGGTGGCCagatct
              Kpn I                                 Xho I           Xba I
```

B

C

(1) 0xG-2

(2) 1xG-9

(3) 2xG-6

(4) 3xG-9

ABIOTIC STRESS TOLERANT TRANSGENIC PLANTS

BACKGROUND OF THE INVENTION

Abiotic stresses, such as drought, extreme temperature, high salinity and nutrient starvation, are major environmental factors that limit plant growth and productivity worldwide. For example, in the United States, approximately 90% of lands are constantly subjected to abiotic stresses, and approximately 70% of the maximal potential yields of major crops are routinely lost due to the unfavorable environmental factors (Boyer (1982), *Science* 218: 443-448). To circumvent environmental stresses, many plants have developed different physiological and biochemical mechanisms to adapt or tolerate stress conditions. Accumulation of low-molecular-weight osmolytes, such sugar alcohols, special amino acids and Gly betaine (Greenway and Munns (1980), *Annu Rev Plant Physiol* 31: 149-190; Yancey et al. (1982), *Science* 217: 1214-1222) or expression of some new proteins, e.g., late embryogenesis abundant (LEA) proteins (Greenway and Munns (1980), above; Yancey et al. (1982), above; Baker et al. (1988), *Plant Mol Biol* 11: 277-291; Dure et al. (1989), *Plant Mol Biol* 12: 475-486; Skriver and Mundy (1990), *Plant Cell* 2: 503-512; Chandler and Robertson, (1994) *Annu Rev Plant Physiol Plant Mol Biol* 45:113-141), have been suggested to play roles in stress tolerance of plants.

Compared with traditional plant breeding, genetic engineering provides a relatively fast and precise means of achieving improved stress tolerance of crop plants. Over-accumulation of osmolytes, stress-regulated transcription factors, transporters that maintain ionic homeostasis, oxidative stress-related proteins, or LEA proteins in transgenic plants have been widely pursued as effective strategies in improving plant tolerance to a broad range of stresses (Bajaj et al. (1999), *Mol Breeding* 5: 493-503; Bartels (2001), *Trends Plant Sci* 6: 284-286; Ho and Wu (2004), In H. T. Nguyen and A. Blum, ed., *Physiology and Biotechology Integration for Plant Breeding*. Marcel Dekker, Inc, New York, N.Y., pp. 489-502). However, under normal environmental conditions, constitutive over-production of these compounds or proteins consumes extra energy and often results in suboptimal growth, altered metabolisms and/or productivity of plants (Goddijn et al. (1997), *Plant Physiol* 113: 181-190; Romero et al. (1997), *Planta* 201:293-297; Kasuga et al. (1999), *Nat Biotechnol* 17: 287-291; Hsieh et al. (2002), *Plant Physiol* 130: 618-626). Thus, it is desirable to generate transgenic plants that synthesize a high level of an osmoprotectant or a protein, or initiate any other stress tolerant mechanisms, only under a stressful condition.

To minimize the negative effects of transgene overepression on growth and productivity while improving stress-tolerance of plants, the use of stress-responsive promoters has been demonstrated to be a promising approach (Su et al. (1998) *Plant Physiol* 117:913-922; Kasuga et al. (1999), *Nat Biotechnol* 17: 287-291; Garg et al. (2002), *Proc Natl Acad Sci USA* 99: 15898-15903; Lee et al. (2003), *Plant Cell Environ* 26: 1181-1190; Fu et al. (2007), *Plant Cell Rep* (in press)).

Abscisic acid (ABA) regulates the expression of many genes that may function in the adaptation of vegetative tissues to several abiotic stresses as well as in seed maturation and dormancy (Himmelbach et al. (2003), *Curr Opin Plant Biol* 6: 470-479; Shinozaki et al. (2003), *Curr Opin Plant Biol* 6: 410-417; Taiz and Zeiger (2006) Chapter 23, In: *Plant Physiology*, 4th edition. Sinauer Associates, Inc., pp. 594-613; Yamaguchi-Shinozaki and Shinozaki (2006). *Annu Rev Plant Biol* 57: 781-803). Many ABA-inducible genes contain a conserved ABA responsive cis-acting element with an ACGT core, designated as ABRE or G box, in their promoters (Guiltinan et al. (1990), *Science* 250:267-271; Skriver et al. (1991), *Proc Natl Acad Sci USA* 88: 7266-7270; Shen et al. (1993), *J Biol Chem* 268:23652-23660). Promoter studies of two barley ABA inducible genes, HVA1 and HVA22, indicated that ABRE and another cis-acting coupling element (CE), together forming an ABA response complex (ABRC), are required for high-level ABA-induced gene transcription (Straub et al. (1994), *Plant Mol Biol* 26: 617-630; Shen and Ho (1995), *Plant Cell* 7: 295-307; Shen et al. (1996), *Plant Cell* 8: 1107-1119).

The ABRC from HVA22 (ABRC1) is composed of ABRE3 or A3 and a downstream coupling element CE1 (A3-CE1). The ABRC from HVA1 (ABRC3) is composed of ABRE2 or A2 and an upstream coupling element CE3 (CE3-A2) (Shen et al. (1996), above). Studies with a barley aleurone transient expression assay system indicated that the ABRE3 (A3) from HVA22 is interchangeable with the ABRE2 from HVA1 for conferring ABA inducible response, suggesting that both ABREs could interact with either CE1 from HVA22 or CE3 from HVA1, while CE1 from HVA22 is not fully exchangeable with CE3 from HVA1 (Shen et al. (1996), above). Nevertheless, the presence of both CE1 and CE3 accompanying ABRE2 (A2) or ABRE3 has a synergistic effect on the absolute activity as well as on the ABA induction of a promoter (Shen et al. (1996), above). Furthermore, in both leaves and aleruone tissues, the HVA1 ABRC3 has a higher absolute activity and is more responsive to ABA as compared to the HVA22 ABRC1 (Shen et al. (1996), above).

Both ABRC1 and ABRC3 have been used to control stress-inducible expression of foreign genes in both monocot and dicot transgenic plants. For example, fusion of one or four copies of ABRC 1 to the rice Act1 minimal promoter confers induced expression of a reporter gene in a transgenic rice plant, a monocot plant, by ABA, dehydration or salt (Su et al. (1998), above). Expression of two *E. coli* trehalose biosynthetic genes in a transgenic rice plant, under the control of a promoter containing four copies of ABRC1, led to accumulation of trehalose and improved growth of these plants under salt, drought and low-temperature stress conditions (Garg et al. (2002), above). Expression of an *Arabidopsis* transcription factor CBF1 in a transgenic tomato plant, a dicot plant, under the control of a promoter containing three copies of ABRC1 fused to the barley α-amylase gene (Amy64) minimal promoter, has also been shown to improve plant growth under chilling, dehydration and salt conditions, while maintain normal growth and productivity under normal growth conditions (Lee et al. (2003), above). Expression of HVA1 in transgenic creeping bentgrass, under the control of a promoter containing two copies of ABRC3, also led to the accumulation of HVA1 and lessened water-deficit injury in these plants (Fu et al. (2007), above).

LEA proteins are a set of proteins highly accumulated in embryos at the late stage of seed development (Dure (1981), *Biochemistry* 20: 4162-4168; Dure (1992), In DPS Verma, ed., *Control of Plant Gene Expression*, CRC Press, Boca Raton, Fla., pp. 325-335). LEA proteins were initially classified into three major groups based on conservation in amino acid sequence domains (Baker et al. (1988), *Plant Mol Biol* 11: 277-291; Dure et al. (1989), *Plant Mol Biol* 12: 475-486). The conserved domains in group 3 LEA proteins are composed of tandem repeats of an 1'-amino acid motif that may form an amphiphilic α-helix structure (Baker et al. (1988), above; Dure et al. (1989), above; Dure (1993), *Plant J* 3: 363-369). The correlation between the LEA protein accumulation and stress tolerance has been demonstrated in a number of plants. For example, levels of group 3 LEA proteins were elevated in seedlings of dehydration tolerant wheat (Ried and Walker-Simmons (1993), *Plant Physiol* 102: 125-131) and roots of ABA and salt tolerant rice (Moons et al. (1995), *Plant Physiol* 107:177-186).

HVA1 is a member of the group 3 LEA proteins identified in barley aleurone, which is specifically expressed in aleurone layers and embryos during late seed development undergoing desiccation (Hong et al. (1988), *Plant Mol Biol* 11: 495-506). The expression of HVA1 is rapidly induced in young seedlings by ABA and several stressful conditions, including dehydration, salt, and extreme temperatures (Hong et al. (1992), *Plant Mol Biol* 18: 663-674; Sutton et al. (1992), *Plant Physiol* 99: 338-340; Straub et al. (1994), *Plant Mol Biol* 26: 617-630). Function of HVA1 in protection against drought, salt and/or osmotic stresses has been demonstrated by transgenic approaches in rice (Xu et al. (1996), *Plant Physiol* 110: 249-257) wheat (Sivamani et al. (2000), *Plant Science* 155: 1-9) oat (Maqbool et al. (2002), *Theor Appl Genet.* 105: 201-208) and bentgrass (Fu et al. (2007), above).

As the world's population increases at a high rate, the improvement of crop productivity remains an important and challenging task. Development of crops that are more tolerant to various abiotic stresses could lead to the use of more new lands for cultivation. There remains a need for development of crops that are more tolerant to various abiotic stresses and new genetic tools that enable such development. The present invention satisfies this need.

BRIEF SUMMARY OF THE INVENTION

It is now discovered that, in a transgenic plant, a stress-responsive promoter comprising CE3 and ABRE2 (A2) from HVA1 ABRC3 and CE1 from HVA22 ABRC1, directs low background expression of a gene under normal growth conditions, but is highly inducible by an abiotic stress, such as ABA, dehydration, salt or cold. Compared with the wild type plant, the transgenic plant that expresses a stress-resistant gene under the control of the stress-responsive promoter is more resistant and/or tolerant to abiotic stresses and exhibits similar or higher growth rate and strength under regular or normal environmental conditions.

In one general aspect, the present invention relates to an isolated nucleic acid molecule comprising a stress-responsive promoter operably linked to a coding region of a stress-resistant gene, or a complement thereof. The stress-responsive promoter comprises, from the 5'-end to the 3'-end of the promoter, in the order of:

(a) the nucleotide sequence of SEQ ID NO: 1;
(b) the nucleotide sequence of SEQ ID NO:2; and
(c) the nucleotide sequence of SEQ ID NO:3;

wherein the last nucleotide residue at the 3'-end of SEQ ID NO:2 is separated from the first nucleotide residue at the 5'-end of SEQ ID NO:3 by about 10 nucleotides in the stress-responsive promoter.

In an embodiment of the present invention, the stress-responsive promoter comprises the nucleotide sequence of SEQ ID NO:5, a sequence herein named as ABRC321.

In another general aspect, the present invention relates to an expression vector comprising a nucleic acid molecule according to embodiments of the invention. The present invention also relates to a recombinant cell comprising a nucleic acid molecule according to embodiments of the invention.

In yet another general aspect, the present invention relates to a transgenic plant comprising a nucleic acid molecule according to embodiments of the invention. In one embodiment, the transgenic plant is a cereal plant. The present invention also relates to a cereal gain produced from a transgenic cereal plant according to embodiments of the present invention, and a preparation for food, produced from a cereal grain according to embodiments of the present invention. According to an embodiment of this aspect of the present invention, the preparation of food is selected from the group consisting of oatmeal, popcorn, brown rice, whole wheat flour, white rice, white bread, and hominy.

In a further general aspect, the present invention relates to a method of obtaining a transgenic plant having enhanced stress tolerance. The method comprises:

(a) transforming a plant cell with a nucleic acid molecule according to an embodiment of the present invention to obtain a recombinant plant cell; and (b) growing the recombinant plant cell obtained in (a) to generate a transgenic plant having enhanced stress tolerance.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

In the drawings.

DETAILED DESCRIPTION OF THE INVENTION

Figure 1:
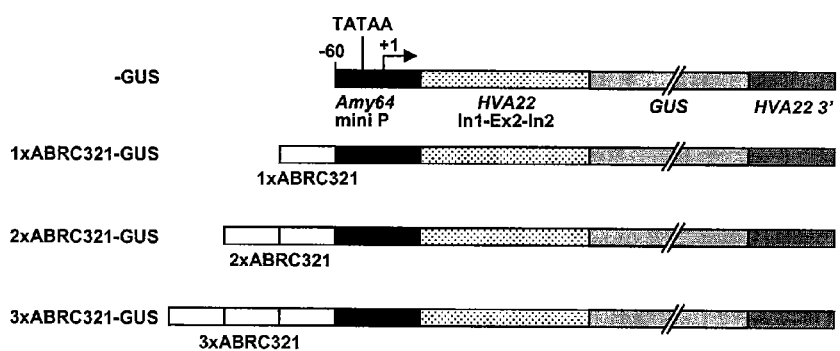
FIG. 1 illustrates: (A) nucleotide sequence of ABRC321 (SEQ ID NO:5), which contains CE3 (SEQ ID NO: 1) and A2 (SEQ ID NO:2) from HVA1 ABRC3 and CE1 (SEQ ID NO:3) from HVA22 ABRC1, and the complement of ABRC321 (SEQ ID NO:14), wherein letters in lowercase indicate nucleotide sequences not derived from HVA1 or HVA22; (B) expression vector constructs containing 0-4 copies of ABRC321 for the expression of GUS protein; and (C) expression vector constructs containing 3 copies of ABRC321 for the expression of HVA1 protein.
Figure 1:
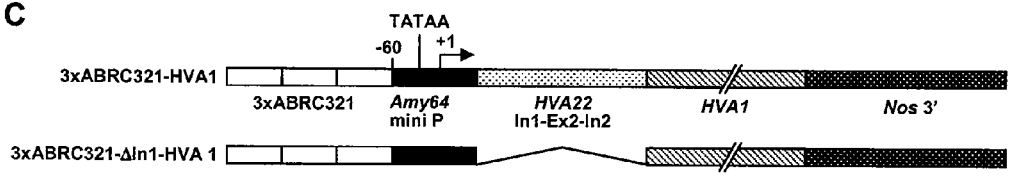

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the term "gene" refers to a segment of DNA involved in producing a functional RNA. A gene includes the coding region, non-coding regions preceding ("5'UTR") and following ("3'UTR") the coding region, alone or in combination. The functional RNA can be an mRNA that is translated into a peptide, polypeptide, or protein. The functional RNA can also be a non-coding RNA that is not translated into a protein species, but has a physiological function otherwise. Examples of the non-coding RNA include, but are not limited to, a transfer RNA (tRNA), a ribosomal RNA (rRNA), a micro RNA, a ribozyme, etc. A "gene" can include intervening non-coding sequences ("introns") between individual coding segments ("exons"). A "coding region" or "coding sequence" refers to the portion of a gene that is transcribed into an mRNA, which is translated into a polypeptide and the start and stop signals for the translation of the corresponding polypeptide via triplet-base codons. A "coding region" or "coding sequence" also refers to the portion of a gene that is transcribed into a non-coding but functional RNA.

As used herein, the term "stress-resistant gene" refers to a gene involved in producing a gene product that confers resistance and/or tolerance to an abiotic stress to a plant. Examples of the stress-resistant gene products include, but are not limited to, stress-regulatory proteins, such as transcription factors, protein kinases, enzymes involved in phosphoinositide metabolism, and enzymes required for the synthesis of the plant hormone abscisic (ABA); or proteins that directly protect cells from stresses, such as enzymes required for biosynthesis of various osmoprotectants and fatty acid metabolisms; chaperones; proteinase inhibitors; ferritin; water channel proteins; sugar and praline transporters; detoxification enzymes; lipid-transfer proteins; transporters that maintain ionic homeostasis; oxidative stress-related proteins; antifreeze proteins (AFPs) or ice structuring proteins (ISPs) that permit the plant survival in subzero environments; heat shock proteins (HSP) whose expression is increased when the plant is exposed to elevated temperatures or other stress; late embryogenesis abundant (LEA) proteins that are expressed at different stages of late embryogenesis in higher plant seed embryos and under certain conditions of abiotic stresses, such as dehydration; proteins involved in a stress-responsive metabolic pathway, such as those for amino acid metabolism, lipid metabolism, or secondary metabolism; proteins involved in photosynthesis, etc. (Phan et al., (2007) *Methods in Enzymol* 428:109-128).

As used herein, a "promoter" refers to a portion of a gene that provides a control point for regulated gene transcription. A promoter can include a binding site for RNA polymerase. A promoter can also include one or more binding sites for one or more transcription factors. A promoter is often upstream of ("5' to") the transcription initiation site of a gene. A promoter is typically adjacent to the transcriptional start site of the gene. However, a promoter can also be located at a distance from the transcriptional start site of the gene.

As used herein, the term "stress-responsive promoter" refers to a promoter that provides a control point for regulated gene transcription in response to an abiotic stress signal. The regulated gene transcription in response to an abiotic stress signal can be achieved by any gene regulation mechanism. For example, a stress-responsive promoter can be involved in gene transcription activated by a signal that is present during an abiotic stress, resulting in gene expression during the abiotic stress. A stress-responsive promoter can also be involved in gene transcription repressed by a signal that is absent during an abiotic stress, thus also resulting in gene expression during the abiotic stress.

The effectiveness of a stress-responsive promoter can be tested in a reporter assay. The stress-responsive promoter can be operably linked to a reporter gene and introduced into a cell, a transgenic plant, or only a portion, i.e., leaves, of a plant. The expression level of the reporter gene in the cell, the transgenic plant, or the portion of the plant, can be analyzed under one or more abiotic stresses. Such expression level indicates the types of abiotic stresses the tested promoter are responsive to, and the degree of responses, etc.

A "reporter gene" refers to a nucleic acid sequence that encodes a reporter gene product. As is known in the art, reporter gene products are typically easily detectable by standard methods. Exemplary suitable reporter genes include, but are not limited to, genes encoding luciferase (lux), β-galactosidase (lacZ), green fluorescent protein (GFP), chloramphenicol acetyltransferase (CAT), β-glucuronidase (GUS), neomycin phosphotransferase, and guanine xanthine phosphoribosyl-transferase proteins.

As used herein, the term "abiotic stress" refers to a stressful condition to a plant caused by a nonliving environmental factor. Examples of abiotic stress include, but are not limited to drought, extremely high or low temperatures, high or low pH, edaphic conditions, high winds, high salinity, nutrient starvation, flooding, anoxia, hypoxia, UV radiation and high light. An abiotic stress can substantially limit plant growth and survival.

As promoters are typically immediately adjacent to the gene in question, positions in the promoter are designated relative to the transcriptional start site, where transcription of RNA begins for a particular gene (i.e., positions upstream are negative numbers counting back from −1, for example −100 is a position 100 base pairs upstream). Conventional notation is used herein to describe polynucleotide sequences. The left-hand end of a single-stranded polynucleotide sequence is the 5'-end, and the left-hand direction of a single-stranded polynucleotide sequence is referred to as the 5'-direction. The left-hand end of a double-stranded polynucleotide sequence is the 5'-end of the plus strand, which is depicted as the top strand of the double strands, and the right-hand end of the double-stranded polynucleotide sequence is the 5'-end of the minus strand, which is depicted as the bottom strand of the double strands. The direction of 5' to 3' addition of nucleotides to nascent RNA transcripts is referred to as the transcription direction. A DNA strand having the same sequence as an mRNA is referred to as the "coding strand." Sequence on a DNA strand which is located 5' to a reference point on the DNA is referred to as "upstream sequence"; sequence on a DNA strand which is 3' to a reference point on the DNA is referred to as "downstream sequence."

As used herein, "operably linked" refers to a functional relationship between two nucleotide sequences. A single-stranded or double-stranded nucleic acid moiety comprises the two nucleotide sequences arranged within the nucleic acid moiety in such a manner that at least one of the two nucleotide sequences is able to exert a physiological effect by which it is characterized upon the other. By way of example, a promoter sequence that controls transcription of a coding sequence is operably linked to that coding sequence. Operably linked nucleic acid sequences can be contiguous, typical of many promoter sequences, or non-contiguous, in the case of, for example, nucleic acid sequences that encode repressor proteins. Within a recombinant expression vector, "operably linked" is intended to mean that the coding sequence of interest is linked to the regulatory sequence(s) in a manner that allows for expression of the coding sequence, e.g., in an in vitro transcription/translation system or in a host cell when the vector is introduced into the host cell.

"Sequence" means the linear order in which monomers occur in a polymer, for example, the order of amino acids in a polypeptide or the order of nucleotides in a polynucleotide.

As used herein, the term "nucleotide sequence", "nucleic acid" or "polynucleotide" refers to the arrangement of either deoxyribonucleotide or ribonucleotide residues in a polymer in either single- or double-stranded form. Nucleic acid sequences can be composed of natural nucleotides of the following bases: T, A, C, G, and U, and/or synthetic analogs of the natural nucleotides. In the context of the present invention, adenosine is abbreviated as "A", cytidine is abbreviated as "C", guanosine is abbreviated as "G", thymidine is abbreviated as "T", and uridine is abbreviated as "U".

As used herein, an "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% or less, and preferably less than 1%, (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

A polynucleotide can have a single strand or parallel and anti-parallel strands. Thus, a polynucleotide may be a single-stranded or a double-stranded nucleic acid. A polynucleotide is not defined by length and thus includes very large nucleic acids, as well as short ones, such as an oligonucleotide.

A "complement of a nucleotide sequence" is a nucleic acid molecule that is sufficiently complementary to the nucleotide sequence so that it can hybridize to the nucleotide sequence thereby forming a stable duplex under high stringency or stringent hybridization conditions. "Stringent hybridization conditions" or "high stringency" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in a medium comprising 4-6× sodium chloride/sodium citrate (SSC) at about 45-65° C., followed by one or more washes in 0.2×SSC and 0.1% SDS at 50-65° C., depending upon the length over which the hybridizing polynucleotides share complementarity.

As used herein, "recombinant" refers to a polynucleotide, a polypeptide encoded by a polynucleotide, a cell, a viral particle or an organism that has been modified using molecular biology techniques to something other than its natural state.

As used herein, a "recombinant cell" or "recombinant host cell" is a cell that has had introduced into it a recombinant polynucleotide sequence. For example, recombinant cells can contain at least one nucleotide sequence that is not found within the native (non-recombinant) form of the cell or can express native genes that are otherwise abnormally expressed, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation. The term encompasses cells that contain the recombinant polynucleotide sequence either on a vector, such as an expression vector, or integrated into a cell chromosome.

Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. It is further understood that the term "recombinant host cell" refers not only to the particular subject cell, but also to the progeny or potential progeny of such a cell. Because certain modifications can occur in succeeding generations due to either mutation or environmental influences, and in such circumstances, such progeny may not, in fact, be identical to the parent cell, but are still included within the scope of the term as used herein.

As used herein, the term "transgenic plant" or "transgenic line" refers to a plant that contains a recombinant nucleotide sequence. The transgenic plant can be grown or derived from a recombinant cell. A transgenic plant includes progeny, clone, or breeding material, such as seeds, thereof the plant.

As used herein, the term "cereal plant" or "cereal crop" refers to a species of true grasses, i.e., Poaceae or Gramineae family in the Class Liliopsida of the flowering plants, or a species of pseudocereals, that is cultivated for its edible grains or seeds. Cereal plants are staple crops grown in greater quantities and provide more energy worldwide than any other type of crop. Cereal grains are a rich source of carbohydrate. Examples of cereal plants include, but are not limited to, plants of maize, rice, wheat, barley, sorghum, millets, oats, rye, triticale, buckwheat, fonio, quinoa, etc.

As used herein, an "expression vector" refers to a nucleic acid molecule that is used to recombinantly express a gene in a target cell. A heterologous or isolated nucleic acid encoding a gene of interest can be or is inserted into an expression vector. The expression vector with the heterologous or isolated nucleic acid can be or is introduced into a host cell. Once the expression vector is inside the cell, the gene product encoded by the heterologous or isolated nucleic acid is produced by the transcription and translation machinery of the host cell. An expression vector typically has for example, an origin of replication sequence allowing replication of the expression vector in the host cell, multiple cloning sites allowing insertion of the heterologous or isolated nucleic acid, a promoter allowing transcription of a gene of interest in the host cell, a heterologous or isolated nucleic acid encoding the gene of interest, a selectable marker gene that encodes a gene product allowing selection of the host cell containing the expression vector from those that do not. The properties, construction and use of expression vectors in the present invention will be readily apparent to those of skill in view of the present disclosure. For example, the expression vector according to embodiments of the present invention can be a plasmid that is replicable in an *agrobacterium* and contains a stress-inducible promoter operably linked to the coding sequence of a stress-resistant gene.

As used herein, a "preparation for food produced from a cereal grain" refers to any preparation of a cereal grain that is to be used as food or for food preparation. Methods are known to those skilled in the art to produce a preparation for food from a cereal grain in view of the present disclosure. In one embodiment, a seed or a cereal grain is milled to remove the chaff, i.e., the outer husks of the seed, to produce a whole grain or a product of whole grain. Examples of whole grain products include, but are not limited to, oatmeal, popcorn, brown rice, and whole wheat flour. In another embodiment, the germ and the bran portions of a whole grain are further removed to create a refined grain product. Examples of the refined grain products include, but are not limited to, white rice, white bread, and hominy, i.e., dried maize (corn) kernels which have been treated with an alkali of some kind.

In one aspect, the present invention relates to an isolated nucleic acid molecule that comprises a stress-responsive promoter operably linked to a coding region of a stress-resistant gene, or a complement thereof. In one embodiment of the present invention, the stress-responsive promoter comprises CE3 and A2 from HVA1 ABRC3 and CE1 from HVA22 ABRC1. For example, the stress-responsive promoter comprises, from the 5'-end to the 3'-end of the promoter, in the order of: (a) the required or core sequence of CE3 as shown in SEQ ID NO: 1; (b) the required or core sequence of A2 as shown in SEQ ID NO:2; and (c) the required or core sequence of CE1 as shown in SEQ ID NO:3. The last residue at the 3'-end of A2 is about 10 nucleotides apart from the first residue at the 5'-end of CE1 on the stress-responsive promoter.

In one embodiment of the present invention, the stress-responsive promoter comprises the nucleotide sequence of SEQ ID NO:4.

In another embodiment of the present invention, the stress-responsive promoter comprises the nucleotide sequence of SEQ ID NO:5, i.e., the ABRC321 sequence.

In yet another embodiment of the present invention, the stress-responsive promoter further comprises an α-amylase minimal (−64 bp) promoter (Amy64 mini P), which comprises the nucleotide sequence of SEQ ID NO:6. Other minimal promoters comprising the core elements for transcription, such as a transcription start site and a binding site for RNA polymerase, can also be used together with CE3 and A2 from HVA1 and CE1 from HVA22 in the present invention. Examples of such other minimal promoters include, but are not limited to, promoters for rice Actin, Ubiquitin and CaMV35S, and alpha-amylase minimal promoter.

In yet another embodiment of the present invention, the stress-responsive promoter comprises one, two, three, or more copies of the ABRC321 promoter and a minimal promoter, such as the Amy64 mini P. The minimal promoter is located to the 3'-end of the ABRC321 promoter. In particular embodiments of the present invention, the stress-responsive promoter comprises a nucleotide sequence selected from the group consisting of: SEQ ID NO:7, SEQ ID NO:8, and SEQ ID NO:9.

As defined above, the stress-resistant gene can be any gene that is involved in a plant's resistance and/or tolerance to an abiotic stress. Particular examples of the stress-resistant genes are trehalose biosynthetic genes. The inducible expression of two E. coli trehalose biosynthetic genes led to accumulation of trehalose and improved growth of transgenic plants expressing them under salt, drought and low-temperature stress conditions (Garg et al. (2002), above). Trehalose biosynthetic genes from other species can also be used. Another specific example of the stress-resistant genes is transcription factor CBF1 gene. The stress inducible expression of Arabidopsis CBF1 gene improved plant growth under chilling, dehydration and salt conditions, while maintain normal growth and productivity under normal growth conditions (Lee et al. (2003), above). CBF1 genes from other species can also be used. Another specific example of the stress-resistant genes is a LEA gene.

In an embodiment of the present invention, the stress-resistant gene encodes a HVA1 protein having the amino acid sequence of SEQ ID NO: 10. In another embodiment, the isolated nucleic acid molecule comprises SEQ ID NO:11, SEQ ID NO: 12, and SEQ ID NO: 13, which comprise respectively 1, 2, and 3 copies of ABRC321, the Amy64 miniP, and a coding sequence of SEQ ID NO:10.

In yet another embodiment of the present invention, the nucleic acid molecule of the invention comprises a complement of a stress-responsive promoter operably linked to a coding region of a stress-resistant gene.

Any of a variety of procedures known in the art, such as those described above, can be used to make and/or isolate a nucleic acid molecule according to embodiments of the invention in view of the present disclosure.

In another general aspect, the present invention relates to an expression vector comprising a nucleotide sequence according to embodiments of the invention. The recombinant expression vectors comprise a nucleic acid according to embodiments of the invention in a form suitable for expression of the nucleic acid in a host cell. It will be appreciated by those skilled in the art that the design of the expression vector can depend on such factors as the choice of the host cell to be transformed, the level of expression of protein desired, etc. The expression vectors according to embodiments of the invention can be introduced into host cells to thereby produce proteins or peptides, including fusion proteins or peptides, encoded by nucleic acids as described herein.

In an embodiment of the present invention, the expression vector is replicable and confers a selective marker in a plant cell. In another embodiment of the present invention, the expression vector is replicable and confers a selective marker in an Agrobacterium, a bacterium known for its ability to transfer nucleic acid between itself and plants. In yet another embodiment of the present invention, the expression vector allows the shuttling or exchange of nucleotide sequences between a plant cell and an Agrobacterium. Such expression vectors can be a modified bacterial tumor-inducing (Ti) plasmid or a bacterial root-inducing (Ri) plasmid. In an embodiment of the present invention, the expression vector comprises the nucleotide sequence of one selected from SEQ ID NOs: 11-13.

Any of a variety of procedures known in the art, such as electroporation, calcium phosphate precipitation, microinjection, nanoparticle-mediated transformation, biolistics-mediated transformation and viral infection, can be used to introduce an expression vector into a host cell in view of the present disclosure.

In another general aspect, the present invention relates to a recombinant cell comprising a nucleotide sequence according to embodiments of the invention. In one embodiment, the recombinant cell is a recombinant plant cell. In another embodiment, the recombinant cell is a recombinant Agrobacterium cell. In another embodiment, the recombinant cell comprises an expression vector according to embodiments of the present invention. In an embodiment of the present invention, the recombinant cell comprises the nucleotide sequence of one selected from SEQ ID NOs:11-13.

Any of a variety of procedures known in the art can be used to construct a recombinant cell according to embodiments of the present invention. For example, a nucleotide sequence according to embodiments of the invention can be introduced into a host cell via a vector. The nucleotide sequence can stay on the vector, separate from the chromosome, in the recombinant cell, such as in a transiently transfected recombinant cell that transiently expresses a gene product encoded by the nucleotide sequence. The nucleotide sequence can also be integrated into the chromosome in the recombinant cell, such as in a stably transfected recombinant cell that stably expresses a gene product encoded by the nucleotide sequence.

In another general aspect, the present invention relates to a transgenic plant comprising a nucleic acid molecule comprising a stress-responsive promoter operably linked to a coding region of a stress-resistant gene according to embodiments of the invention. In one embodiment, the transgenic plant comprises the nucleotide sequence of one selected from SEQ ID NOs: 11-13. In another embodiment, the transgenic plant is a transgenic cereal plant, preferably a transgenic rice plant.

In one embodiment, a transgenic plant according to embodiments of the present invention stably expresses a gene encoded by a recombinant nucleic acid molecule according to embodiments of the invention. In such a transgenic plant, the recombinant nucleic acid molecule is stably transformed or transfected into a plant cell and has become integrated into the chromosome of the plant cell so that the recombinant nucleic acid molecule is inherited by daughter cells of the plant cell through chromosome replication.

Any of a variety of procedures known in the art can be used to engineer a stable transgenic plant in view of the present disclosure. In one embodiment of the present invention, the transgenic plant is constructed by transforming a tissue of a plant, such as a protoplast or leaf-disc of the plant, with a recombinant *Agrobacterium* cell comprising a nucleic acid molecule according to embodiments of the present invention, and generating a whole plant using the transformed plant tissue. In another embodiment of the present invention, flowers of a plant can be dipped in a culture of recombinant *Agrobacterium* cell comprising a nucleic acid molecule according to embodiments of the present invention. After the bacterium transforms the germline cells that make the female gametes, seeds can be screened for markers carried by the nucleic acid molecule according to embodiments of the present invention. Transgenic plants are then grown out of the seeds.

In another embodiment of the present invention, a nucleic acid molecule according to embodiments of the invention can be introduced into a plant via gene gun technology, particularly when transformation with a recombinant *Agrobacterium* cell is less efficient in the plant. The gene gun technology, also referred to as biolistics, delivers genetic information via an elemental particle of a heavy metal coated with plasmid DNA. This technology is able to transform almost any type of plant cells.

In another embodiment, a transgenic plant according to embodiments of the present invention transiently expresses a gene encoded by a recombinant nucleic acid molecule according to embodiments of the invention. Any of a variety of procedures known in the art can be used to engineer such a transgenic plant in view of the present disclosure. In one embodiment, a recombinant nucleic acid molecule according to embodiments of the invention can be introduced into a transgenic plant by particle bombardment, a specific example of which is described below in the examples. In another embodiment, the method of agroinfiltration can be used to allow transient expression of genes in a plant. In the method, for example, a recombinant nucleic acid molecule according to embodiments of the invention is first introduced into a strain of *Agrobacterium* to generate a recombinant *Agrobacterium* cell. A liquid suspension of the recombinant *Agrobacterium* is then injected into the airspaces inside a plant leaf. Once inside the leaf, the recombinant *Agrobacterium* transforms the gene of interest to a portion of the plant cells and the gene is then transiently expressed. As compared to traditional plant transformation, the method of agroinfiltration is speedy and convenient.

The transgenic plant according to embodiments of the present invention can be both monocot and dicot transgenic plants.

In another aspect, the present invention relates to a method of obtaining a plant having enhanced stress tolerance. The method comprises (a) transforming a plant cell with a nucleic acid molecule according to embodiments of the present invention to obtain a recombinant plant cell; and (b) growing the recombinant plant cell obtained in (a) to generate a transgenic plant having enhanced stress tolerance.

In another aspect, the present invention relates to a preparation for food produced from a transgenic cereal grain according to embodiments of the present invention. The present invention also relates to a cereal gain produced from a transgenic cereal plant according to embodiments of the present invention, and a preparation for food, produced from a cereal grain according to embodiments of the present invention. According to an embodiment of this aspect of the present invention, the preparation of food is selected from the group consisting of oatmeal, popcorn, brown rice, whole wheat flour, white rice, white bread, and hominy. Methods known in the art can be used to obtain the cereal grains and preparations for food in view of the present disclosure.

In a preferred embodiment of the present invention, the preparation for food is the brown rice, which does not include the recombinant protein encoded by the stress-resistant gene, such as the HVA1. The recombinant protein, such as HVA1, may be restricted in embryos and aleurone layers, which can be removed as germ and bran during milling for brown rice.

The present invention is further illustrated by the following examples, which are in no way intended to limit the scope of the present invention.

Materials and Methods

Plant Materials

Rice cultivar *Oryza sativa* L. cv Tainung 67 was used for all experiments. Plasmids were introduced into *Agrobacerium tumefaciens* strain EHA101 and rice transformation was performed as described (Chen et al., 2002). Transgenic rice plants were grown in a greenhouse until seeds were harvested. Transgenic rice seeds were germinated in water for 5 days and seedlings were grown in hydroponic solution at 28° C. in an incubator with 12 hr daily light prior to and after various treatments unless otherwise indicated.

Plasmids

Plasmid pAHC18 contains the luciferase (Luc) cDNA fused between the Ubi promoter and the Nos terminator (Bruce et al., 1989). Plasmid MP64 contains the barley Amy64 minimal promoter (−60 relative to the transcription start site) and its 5' untranslated region (+57 relative to the transcription start site), HVA22 intron 1-exon 2-intron 2, the GUS coding region, and the HVA22 3' untranslated region (Shen and Ho, 1995). Plasmid QS115 contains a copy of HVA22 ABRC1 fused upstream of the Amy64 minimal promoter in plasmid MP64 (Shen and Ho, 1995).

Plasmid Construction

Two 56-bp complementary oligonucleotides, containing the CE3 and A2 elements from the HVA1 promoter and the CE1 element from the HVA22 promoter (Shen et al., 1996) and restriction sites KpnI, XhoI and XbaI were synthesized, annealed, and designated as ABRC321 (FIG. 1A). ABRC321 was self-ligated in two and three copies in correct orientations. For expression of GUS under the control of ABRC321, one to three copies ABRC321 were then inserted into the XbaI site in MP64, so that the ABRC321 was fused upstream of the barley Amy64 minimal promoter, generating constructs 1×ABRC321-GUS, 2×-ABRC321-GUS and 3×ABRC321-GUS (FIG. 1B). For expression of HVA1 under the control of ABRC321, GUS cDNA in construct 3×ABRC321-GUS was replaced with HVA1 cDNA, generating construct 3×ABRC321-HVA1 (FIG. 1C). The intron 1 of HVA22 was deleted from construct 3×ABRC321-HVA1, generating construct 3×ABRC321-ΔIn1-HVA1 (FIG. 1C).

Barley Aleurone Tissue Transient Expression Assay

Particle bombardment of the barley (*Hordeum vulgare*) aleurone tissue (embryoless half seeds) and transient assay of GUS were performed essentially as described by Lanahan et al. (Lanahan et al., 1992) and (Cercos et al., 1999). The barley aleurone tissue were co-bombarded with reporter and internal control plasmids at a ratio of 1:1. Bombarded barley embryoless half-seeds were incubated in a buffer (20 mM each of $CaCl_2$ and sodium succinate, pH 5.0) containing or lacking 100 µM ABA for 16 h, and luciferase or GUS activity determined. All the bombardments were repeated for at least four times.

Rice Transformation

Plasmids were introduced into *Agrobacterium tumefaciens* strain EHA101 and rice transformation was performed as described (Chen et al., 2002).

GUS Activity Assay

Total proteins were extracted from 8 bombarded barley embryoless half seeds with 0.8 ml, of CCLR buffer [100 mM KH2(PO$_4$), pH 7.8, 1 mM EDTA, 10% (v/v) glycerol, 1% (v/v) Triton X-100, 7 mM β-mercapatoethanol], and 100 and 50 μl of extracted samples were used for luciferase and GUS activity assays, respectively, with methods as described (Lu et al., 1998). The protein concentration was determined with a Coomassie protein assay reagent (Pierce, Rockford, Ill.). Because transfection efficiency varies from sample to sample using this method, the enzyme activity of an internal control pAHC18 (containing the Ubi-Luc construct) was used to normalize the reporter enzyme activity.

GUS Activity Staining Assay

Mature transgenic seeds were cut longitudinally and incubated in water containing or lacking 100 μM ABA at 28° C. for 16 h and subjected to histochemical staining with a buffer (0.1 M Na$_3$PO$_4$, pH 7.0, 10 mM EDTA, 0.1% (v/v) Triton X-100, 0.5 mM potassium ferricyanide, pH 7.0 and 1 mM X-glucuronide) at 37° C. as described (Jefferson et al., 1987). After GUS staining, leave samples were incubated in 70% ethanol at 65° C. for 1 h to remove chlorophyll.

Protein Gel Blot Analysis

Total soluble proteins were extracted from rice samples with extraction buffer containing 100 mM K-Phosphate buffer, 1 mM EDTA, 10% (v/v) Glycerol, 1% (v/v) Triton X-100, 7 mM β-mercaptoethanol, 100 mM NaF, 1 mM NaVO$_3$, 1 mM Na$_3$VO$_4$, 10 mM Na$_4$P$_2$O$_7$, 10 mM NEM, and 1× Protease inhibitor cocktail (Complete, Roche, Grenzacherstrasse, Switzerland). Total soluble proteins (60 μg) were separated by 10% SDS-PAGE and blotted onto NC membrane (Hybond-ECL, Amersham Biosciences, Piscataway, N.J.). Protein gel blot analysis was performed as described (Yu et al., 1991). Polyclonal rabbit anti-HVA1 antibodies (Hong et al., 1992) were diluted at 1:2500 or 1:5000. HRP-conjugated anti-rabbit IgG (Amersham Biosciences) were used as a secondary antibody. Protein signals were detected by chemiluminescence using ECL (Amersham Biosciences).

Dehydration of Seedlings

For dehydration test, 10-day-old seedlings were planted in small pots containing 330 g of soil, grown in a 28° C. growth chamber. Pot soil was air-dried slowly for 6 days. Pots were then transferred to a bigger container and re-watered until soil was completely submerged in water.

Results

A Composite Promoter Comprising ABRC321 is ABA-Inducible.

An oligonucleotide containing CE3 and A2 from HVA1 ABRC3 and CE1 from HVA22 ABRC1, was designated and synthesized as ABRC321, which is illustrated in (FIG. 1A). Its complete complement was also designated and synthesized. In ABRC321, A2 and CE1 were separated by about 10 bp in order to confer high ABA induction as suggested (Shen et al., 2004). To determine how effectively ABRC321 responds to ABA, the reporter gene GUS (2 kb) was fused downstream of 0-4 copies of ABRC321 (56 bp each), the Amy64 minimal promoter (99 bp), and the intron1-exon2-intron2 of HVA22 (240 bp), followed by a HVA22 terminator (3') (120 bp) (FIG. 1B).

The GUS activity was determined through the barley aleurone layer transient expression assay system. Barley aleurone layers were transiently transfected with various plasmids shown in FIG. 1B by particle bombardment. The transfected barley aleurone layers were incubated with (+) or without (−) 100 μM ABA for 16 hr, and the GUS activity was analyzed. The GUS activity controlled by a promoter containing the HVA22 ABRC1 (Shen et al., 1993) was also determined for comparison.

Figure 2:
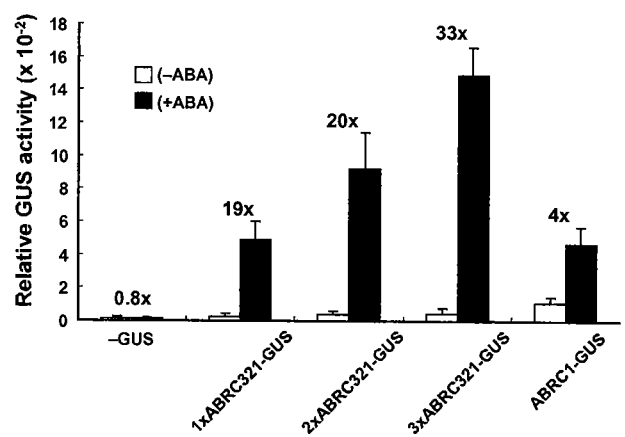
FIG. 2 illustrates results from barley aleurone layer transient expression assays, showing that ABRC321 is ABA inducible in transiently transfected barley aleurone layers, wherein the fold of induction (x) of GUS activity by ABA in each transfected barley aleurone layers is shown, and the error bars indicate standard error of three replicate experiments for each of the constructs.

As shown in FIG. 2, in the absence of ABA, the GUS activity was very low and only slightly increased with the increase of the copy number of ABRC321. In contrast, in the presence of ABA, the GUS activity under the control of promoters containing 1, 2 and 3 copies of ABRC321 were induced 19-, 20-, and 33-fold, respectively. The GUS activity under the control of the Amy64 minimal promoter lacking ABRC321 was not induced by ABA. In the presence of ABA, although the GUS activity under the control of the HVA22 ABRC1 was similar to that under the control of 1 copy of ABRC321, its induction by ABA was only 4-fold, due to the high background activity in the absence of ABA.

Figure 3:
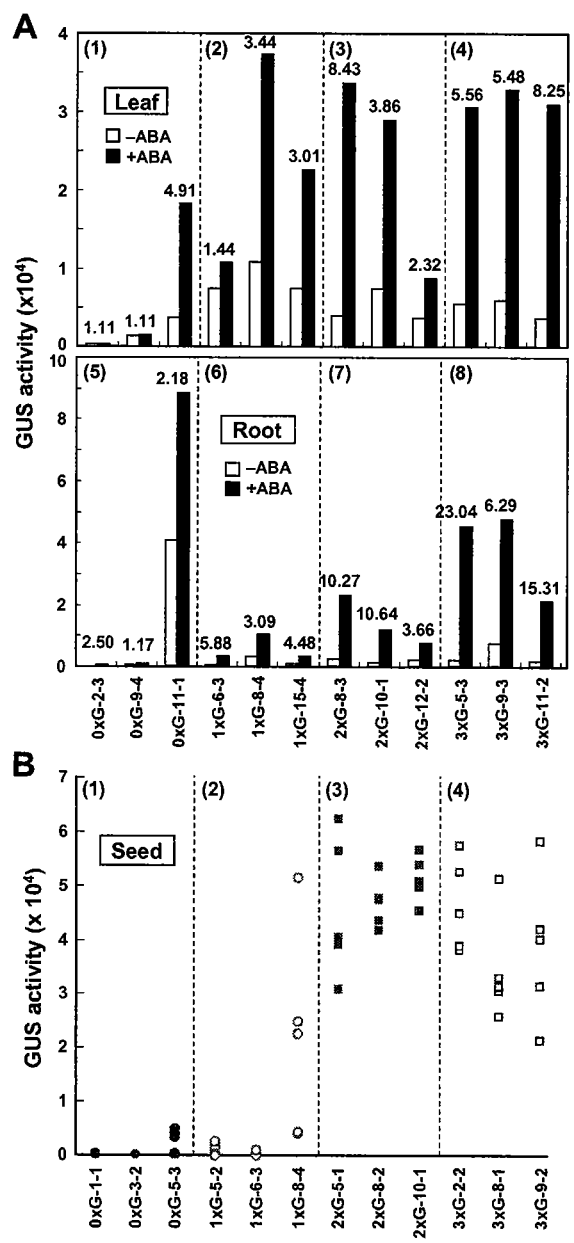
FIG. 3 illustrates results from expression assays, showing that ABRC321 confers high level ABA induction and transcription strengths to a minimal promoter in transgenic rice stably transfected with the GUS gene controlled by 0-3 copies of ABRC321, designated 0×G-, 1×G-, 2×G-, and 3-×G-, respectively, in the figures: (A) GUS activity assayed from leaves: panels (1)-(4); and roots: panels (5)-(8), of 10-day-old T2 seedlings of three stably transfected transgenic rice lines after the leaves and roots were incubated in water with (+) or without (−) 100 μM ABA for 16 h; and (B) GUS activity assayed from mature seeds of the three transgenic rice lines in the absence of ABA, panels (1)-(4)

Constructs containing 1-3 copies of ABRC321, e.g., constructs shown in FIG. 1B, were subcloned into a binary vector and used for rice transformation to generate a stably transfected transgenic plant. GUS activities in leaves, roots and seeds of T2 transgenic rice were determined. Results shown in FIG. 3 with three representative transgenic lines indicated that positions of transgene insertion site in the rice genome may affect promoter activities. The GUS activity in leaves and roots under the control of promoter lacking ABRC321 was hardly or only slightly enhanced by ABA, except in transgenic line 0×G-11-1, which had significantly higher background activity even in the absence of ABA (FIG. 3 A, panel 1). The GUS activity in leaves and roots was significantly enhanced by ABA with promoters carrying 1-3 copies of ABRC321, and generally, the fold of induction was higher with the promoter carrying 3 copies of ABRC321 (FIG. 3A, panels 2-4).

Studies with both barley aleurone transient and rice stable transgene expression assays suggested that 3 copies of ABRC321 confer the strongest activity as well as the highest ABA inducibility to the Amy64 minimal promoter compared to 0-2 copies of ABRC321.

ABRC321 Confers Seed-Specific Activity to a Minimal Promoter.

GUS activities were detected in transgenic seeds even in the absence of ABA (FIG. 3B). The GUS activity in mature T2 seeds under the control of the promoter lacking or containing only 1 copy of ABRC321 was generally relatively low (FIG. 3B, panels 1-2) as compared with those under the control of promoters containing 2 or 3 copies of ABRC321 (FIG. 3B, panels 3-4). However, high GUS activity was detected in some seeds of a transgenic line 1×G-8-4, even though it carries a promoter having only 1 copy of ABRC321 (panel (2) of FIG. 3B). It was noted that the GUS activity was also high in leaves of this transgenic line (panel (2) of FIG. 3A). The high GUS activity in this transgenic line could be due to the positional effect of transgene insertion in the rice genome.

Figure 4:
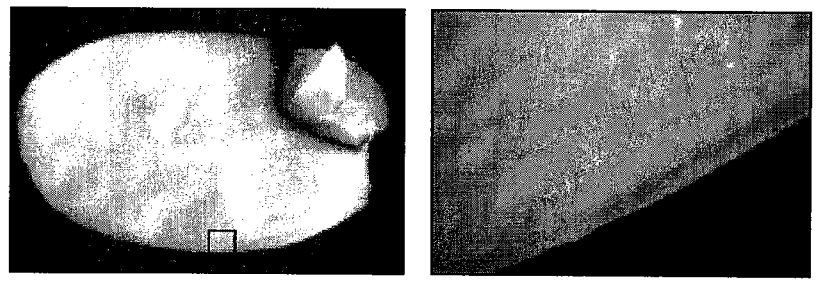
FIG. 4 shows images from GUS activity staining assay of mature T2 transgenic rice seeds carrying stably transfected GUS gene controlled by 1-3 copies of ABRC1, wherein images in the right panels of (1)-(4) show higher magnification of boxed areas in the left panels of (1)-(4), and the abbreviations are: Al, aleurone layer; C, coleoptile; Em, embryo; En, endosperm; P, pericarp; R, radicle; S, scutellum and Sc, seed coat.
Figure 4:
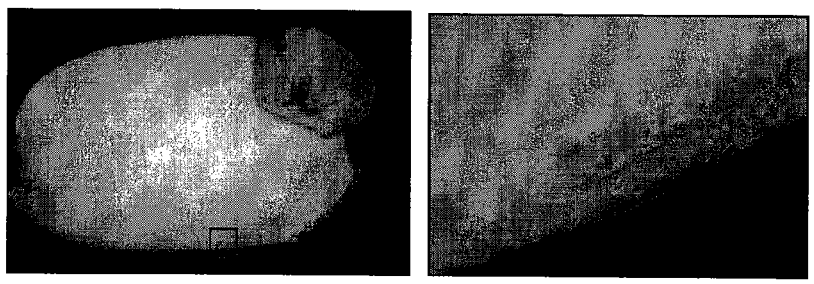
Figure 4:
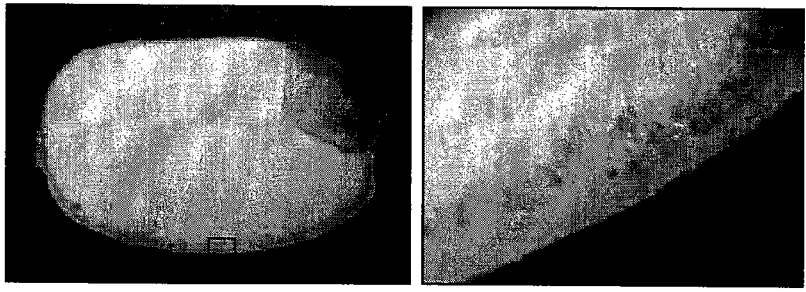
Figure 4:
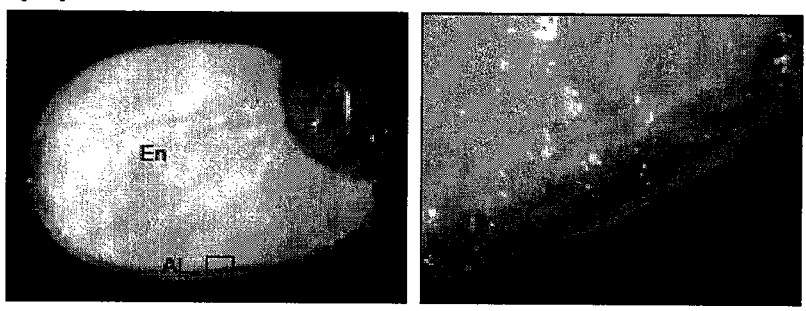

The GUS activity staining assay was performed. Mature T2 transgenic rice seeds, each carrying the GUS gene controlled by 1-3 copies of ABRC321, were cut longitudinally to two halves and stained for GUS activity. The photos in FIG. 4 showed that GUS expression under the control of the Amy64 minimal promoter lacking ABRC321 was detected mainly in the scutellum (FIG. 4, panel 1). GUS expression was also detected in the embryo and aleurone layer with the promoter carrying ABRC321 (FIG. 4, panels 2-4).

These studies demonstrated that the Amy64 minimal promoter confers scutellum specific expression, while ABRC321 confers embryo and aleurone tissue expression to the Amy64 minimal promoter.

3×ABRC321 Controls ABA-Inducible Accumulation of HVA1 in Vegetative Tissues of Transgenic Rice.

With a goal of enhancing the stress tolerance of transgenic rice, 3 copies of ABRC321 were fused with the HVA1 cDNA (630 bp), generating the construct 3×ABRC321-HVA1 (FIG. 1C). The intron1-exon2-intron2 of HVA22 was previously shown to contain information necessary for the ABA response of HVA22, and the intron1 along has a dramatic effect on the ABA induction of HVA22 (Shen et al., 1993). To test whether the intron1 affects the expression of HVA1 operably linked to 3×ABRC321, the intron1 in the construct 3×ABRC321-HVA1 was deleted, generating 3×ABRC321-ΔIn1-HVA1 (FIG. 1C). The constructs also contain a terminator Nos 3' (300 bp) following the HVA1 or ΔIn1-HVA1 cDNA. The two promoter constructs were then delivered into the rice genome and several independent transgenic plants were generated.

Because ABRC321 composite promoters were inducible by ABA in vegetative tissues (FIG. 3A), ABA inducible accumulation of HVA1 in leaves of transgenic rice was determined. T1 seeds of 10 transgenic lines, 5 transformed with 3×ABRC321-HVA1 and 5 with 3×ABRC321-ΔIn1-HVA1, were germinated in water containing 25 μg/ml of hygromycin. Seedlings were treated with or without 100 μM ABA for 16 hours. Total proteins were extracted from leaves of these plants and subjected to protein gel blot analysis using the anti-barley HVA1 antibodies (dilution 1:2500). Copy number of HVA1 gene on the cell chromosome was determined by genomic DNA gel blot analysis using the HVA1 DNA as a probe.

Figure 12:
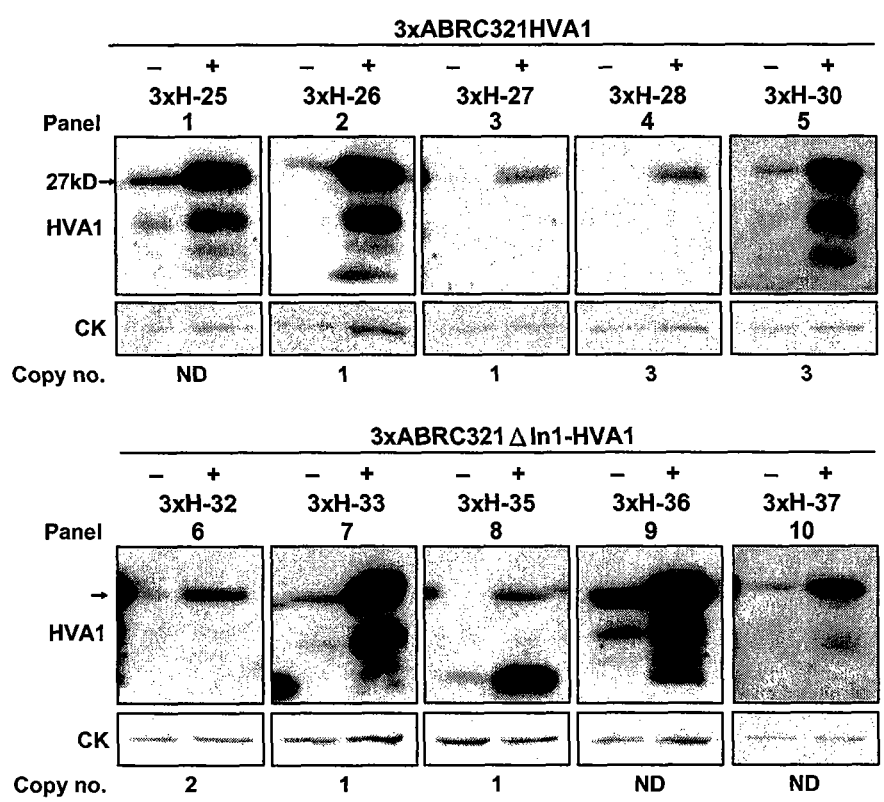
FIG. 12 illustrates results from protein gel blot analyses, showing that intron 1 of HVA22 may not be necessary for the ABA induction of gene expression in transgenic rice; Actin (CK) was used as a loading control, and ND means not determined.

As shown in FIG. 12, accumulation of the 27 kD HVA1 protein (Hong et al., 1988) was detected upon ABA induction, with levels varied from line to line regardless of the presence or absence of intron 1 in the construct. The varied levels of HVA1 protein in the transgenic lines could be due to positional effect of transgene insertion. The transgene copy number did not appear to correlate with the expression level of HVA1. Results shown in FIG. 12 indicate that the intron 1 in the construct is probably not necessary for the ABA induction of gene expression in transgenic rice.

To demonstrate that the expression of HVA1 in progenies was consistently induced by ABA, levels of HVA1 in leaves and roots of seedlings of three T2 homozygous transgenic lines were determined. Three ten-day-old T2 seedlings, each of three homozygous transgenic lines that carry 3×ABRC321-HVA1, as well as a non-transformant (NT), were treated with (+) or without (−) 100 μM ABA for 16 h. Total proteins were extracted from leaves and roots of the plants and subjected to protein gel blot analysis using anti-barley HVA1 antibodies.

Figure 5:
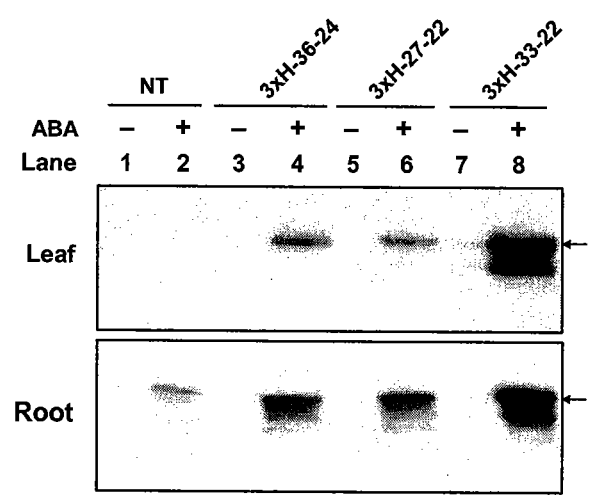
FIG. 5 illustrates results from protein gel blot analyses, showing that 3×ABRC321 controls ABA-inducible accumulation of HVA1 in vegetative tissues, leaf and root, of transgenic rice stably transfected with 3×ABRC321-HVA1, wherein arrows indicate the protein band corresponding to the 27 kD HVA1 protein.

As shown in FIG. 5, in NT seedlings, accumulation of HVA1 was not detected in leaves regardless of the presence or absence of ABA, but was detected in roots in the presence of ABA, which could be due to the presence of endogenous rice HVA1 homolog (lane 2). Amino acid sequence of the endogenous rice HVA1 homolog is highly homologous to the barley HVA1, consequently, the accumulation of the endogenous rice HVA1 homolog could be detected with the anti-barley HVA1 antibodies. In leaves and roots of transgenic seedlings, accumulation of HVA1 was barely detectable in the absence of ABA but was significantly enhanced in the presence of ABA (FIG. 5, lanes 3-8).

ABRC321 Controls Development-Dependent Accumulation of HVA1 in Transgenic Rice Seeds.

To determine whether expression of HVA1 in transgenic rice seeds is developmentally regulated, a T2 homozygous transgenic rice line carrying 3×ABRC321-HVA1, as well as a non-transformant (NT), were grown in pot soil in greenhouse. Flowers were collected 7 days before (−) anthesis and developing seeds were collected 1, 10 and 21 day after (+) anthesis. Total proteins were extracted from the flowers and seeds and were subjected to protein gel blot analysis using the anti-barley HVA1 antibodies (diluted 1:2500). As shown in FIG. 6A, the endogenous rice HVA1 homolog was detected in NT seeds at +21 day of anthesis (DOA) (lane 4); and accumulation of HVA1 in one representative transgenic line was detected as early as +10 DOA, and at higher level at +21 DOA as compared with the NT seeds (lanes 7 and 8).

The results shown in FIG. 6A suggest that ABRC321 confer earlier HVA1 accumulation than the NT during seed development, and transgenic seeds accumulate both endogenous rice HVA1 homolog and recombinantly overexpressed HVA1 as they reach maturation.

Previous GUS activity staining assays indicated that ABRC321 was highly active in embryos (FIG. 4). Accumulation of HVA1 in embryos of several transgenic lines was determined. Five embryos each were collected from mature seeds of several T2 homozygous transgenic lines carrying 3×ABRC321-HVA1. As shown in FIG. 6B, significantly higher levels of HVA1 accumulation in embryos of most transgenic lines were detected as compared with the NT.

To determine whether HVA1 accumulated during germination, mature seeds of two T2 transgenic lines carrying 3×ABRC321-HVA1 were germinated in water for various lengths of time, up to 168 hrs. (7 days). Three germinating seeds or seedlings were collected at each time point. Total proteins were extracted from the entire germinating seeds (mainly from the embryos and aleurone layers) and subjected to protein gel blot analysis using the anti-barley HVA1 antibodies (diluted 1:2500). As shown in FIG. 6C, HVA1 disappeared gradually after seed imbibition, similar to that observed for the endogenous rice HVA1 homolog in NT (FIG. 6C).

Figure 6:
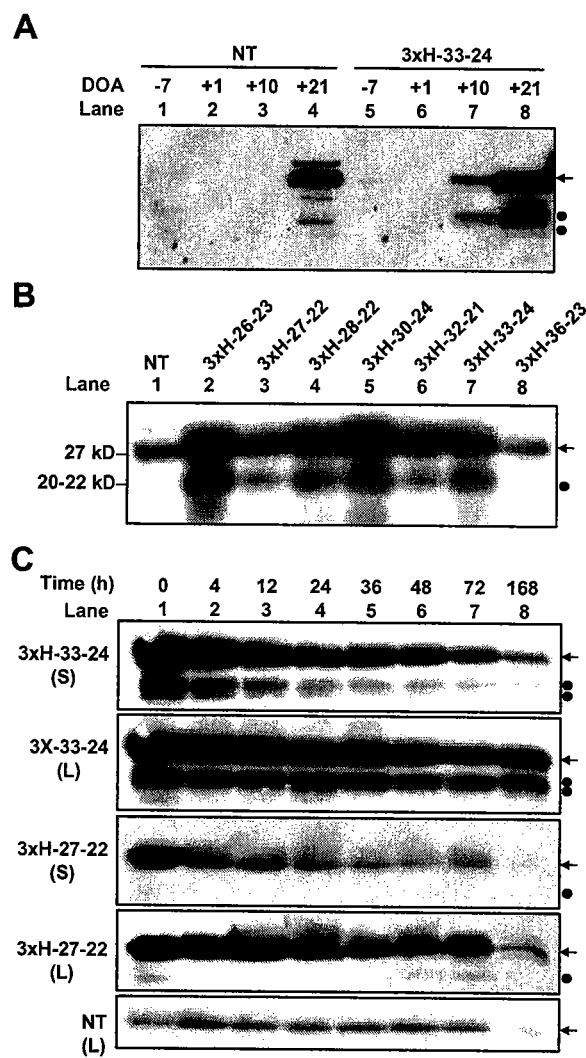
FIG. 6 illustrates results from protein gel blot analyses, showing that 3×ABRC321 controls development-dependent accumulation of HVA1 in transgenic rice seeds during seed development: (A) accumulation of HVA1 in developing seeds; (B) accumulation of HVA1 in embryos from mature seeds; and (C) accumulation of HVA1 after germination, wherein S indicates short and L indicates long exposure of the autography, arrows indicate the 27 kD HVA1 and dots indicate two smaller proteins of 20 and 22 kD.

Smaller proteins, with molecular weights of 20-22 kD, were frequently detected in samples derived from transgenic leaves, roots and seeds from the protein gel blot analyses (FIG. 5 and FIG. 6). These smaller proteins could be degraded forms of HVA1, as their accumulations followed the accumulation pattern of the 27 kD HVA1 and correlated with the abundance of HVA1 in transgenic rice tissues examined. The smaller proteins could be better visualized in some batches of protein preparation than the others.

ABRC321 Controls Multiple Stress-Inducible Accumulation of HVA1 in Vegetative Tissues of Transgenic Rice.

As mentioned in the introduction, expressions of both HVA1 and HVA22 are inducible by ABA, dehydration, salt, and extreme temperatures. Stress test was performed to determine whether the promoter containing ABRC321 was inducible by various stresses in transgenic plants. Ten-day-old seedlings of a T2 homozygous transgenic rice line (3×H-33-24), which carries 3×ABRC321-HVA1, were subjected to stress treatment with 100 μM ABA, 200 mM NaCl, 4° C. temperature or dehydration for various lengths of time. Three seedlings were collected at each time points after treatment with each indicated stress. Total proteins were extracted from the leaves and subjected to protein gel blot analyses using the anti-barley HVA1 antibodies (diluted 1:5000). FIG. 7A shows that under each stress condition tested, the level of HVA1 in leaves increased with time up to 20 hours tested.

Figure 7:
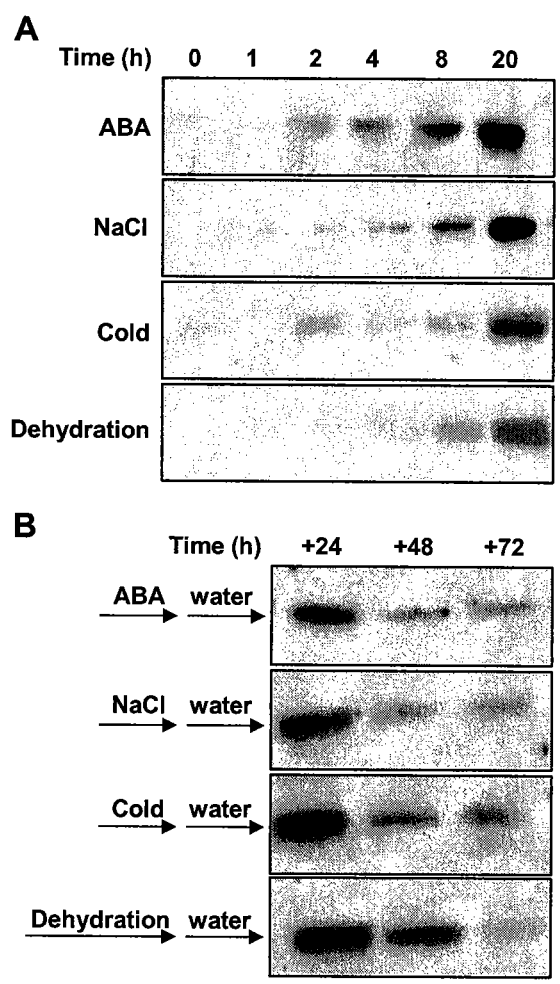
FIG. 7 illustrates results from protein gel blot analyses, showing that 3×ABRC321 controls multiple stress-inducible accumulation of HVA1 in leaves of ten-day-old seedlings of T2 homozygous transgenic rice line (3×H-33-24): (A) accumulation of HVA1 after the seedlings were subjected to indicated stressful conditions for various length of time; (B) accumulation of HVA1 after the seedlings were subjected to indicated stressful conditions for 20 hours and were subsequently transferred to water at 28° C. for additional (+) various lengths of time.

To determine the effect upon relief from a stress condition, ten-day-old seedlings of a T2 homozygous transgenic rice line (3×H-33-24) were subjected to various stress treatments as described above for 20 hours. The stressed seedlings were then transferred to water at 28° C. The level of HVA1 in leaves was assayed at various time points after the stressed seedlings was transferred to water at 28° C. As shown in FIG. 7B, the level of HVA1 decreased gradually after relief from stress conditions. The smaller proteins of 20-22 KD were not detected in the assay shown in FIG. 7 due to the high-fold dilution of the anti-barley HVA1 antibodies The results in FIG. 7 indicate that ABRC321 is sufficient for increasing HVA1 expression in leaves of transgenic rice in response to multiple stresses, and such increased expression is deregulated under non-stress conditions.

Overexpression of HVA1 Enhances Dehydration Tolerance of Transgenic Rice.

Experiments were performed to determine whether overexpression of HVA1 confers dehydration tolerance of transgenic rice. Ten 10-day-old seedlings, each of three T2 homozygous transgenic lines, were grown in soil in the same shallow weighing dish (14.2 cm$^2$). The three transgenic lines were known to express various levels of HVA1 (FIG. 12). These plants were subjected to 5 cycles of 2-day watering (hydration) and 5-day air dry (dehydration) of soil at 28° C. in a growth chamber. In each cycle, soil was saturated with water at the first day of watering and almost completely dried at the fifth day of air drying. Plant survival rates were determined by counting the number of plants that grew at the end of the 5$^{th}$ dehydration cycle. The experiment was repeated three times. Plant heights were also measured by measuring the length of the longest leaves on the top of each plant at the end of the 5$^{th}$ dehydration cycle.

Figure 8:
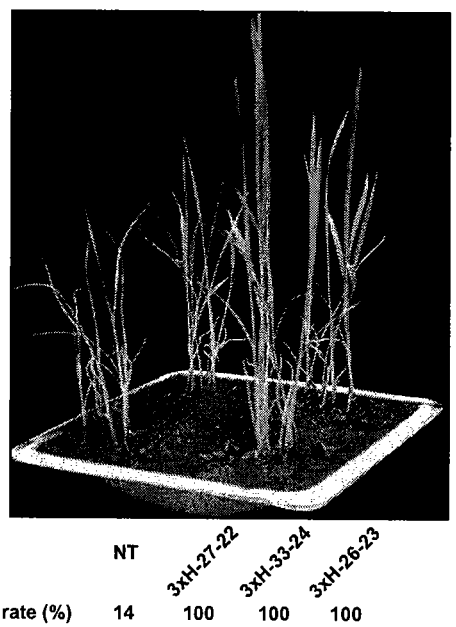
FIG. 8 illustrates that overexpression of HVA1 enhances dehydration tolerance of transgenic rice plants: (A) morphology and survival rates of the plants after 5 cycles of dehydration and hydration, similar results were obtained from three repeating experiments; (B) plant heights at the end of the 5$^{th}$ dehydration cycle, wherein error bars indicate standard error of heights of seven seedlings; (C) protein gel blot analysis of accumulation of HVA1 in the non-transformant (NT) and transgenic plants with (+) or without (-) dehydration treatment, wherein Actin (CK) was used as a loading control.
Figure 8:
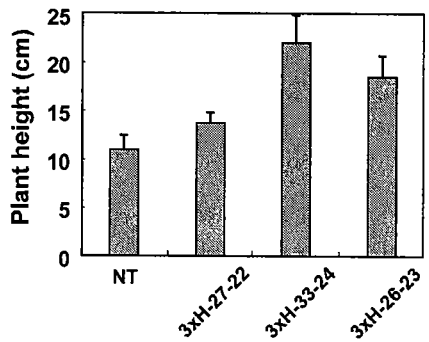
Figure 8:
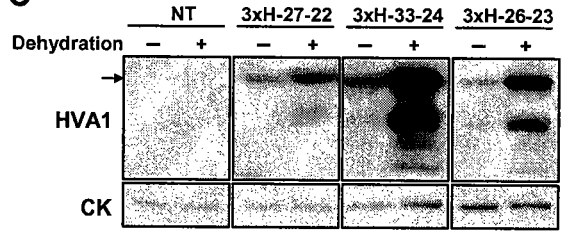

Morphology and survival rates of the plants after 5 cycles of dehydration and hydration are shown in FIG. 8A. In general, the three transgenic lines appeared bigger in size than the non-transformant (NT) control. The survival rate was 14% for NT and was about 86-100% for the three transgenic lines (FIG. 8A). The average plant heights were 11 cm for NT and 13.5, 18 and 22 cm for the three transgenic lines (FIG. 8B).

The accumulation of HVA1 after dehydration was also analyzed. Ten-day-old seedlings of the same three transgenic lines used in the dehydration tolerance assay described above were air-dried at 28° C. in a growth chamber for 4 h. Total proteins were extracted from leaves and subjected to protein gel blot analysis using the anti-barley HVA1 antibodies (dilution 1:2500). Actin (CK) was used as a loading control. It cross-reacted with the HVA1 antibodies but its accumulation levels remained constant regardless of whether the plants were under dehydration treatment or not. FIG. 8C shows that the increased survival rates and plant heights of transgenic lines were correlated with their capability of HVA1 accumulation after dehydration.

Overexpression of HVA1 Enhances Salt Tolerance of Transgenic Rice.

Experiments were performed to determine whether overexpression of HVA1 confers salt tolerance of transgenic rice. T2 seedlings of transgenic lines used for dehydration experiments described above were germinated in 100 or 200 mM NaCl for 5 days and transferred to water to recover for 14 days. Plant survival rates were determined by counting the number of plants that grew at the end of the experiment. Plant heights were determined by measuring the length of the longest leaves on the top of each plant at the end of the experiment.

Figure 9:
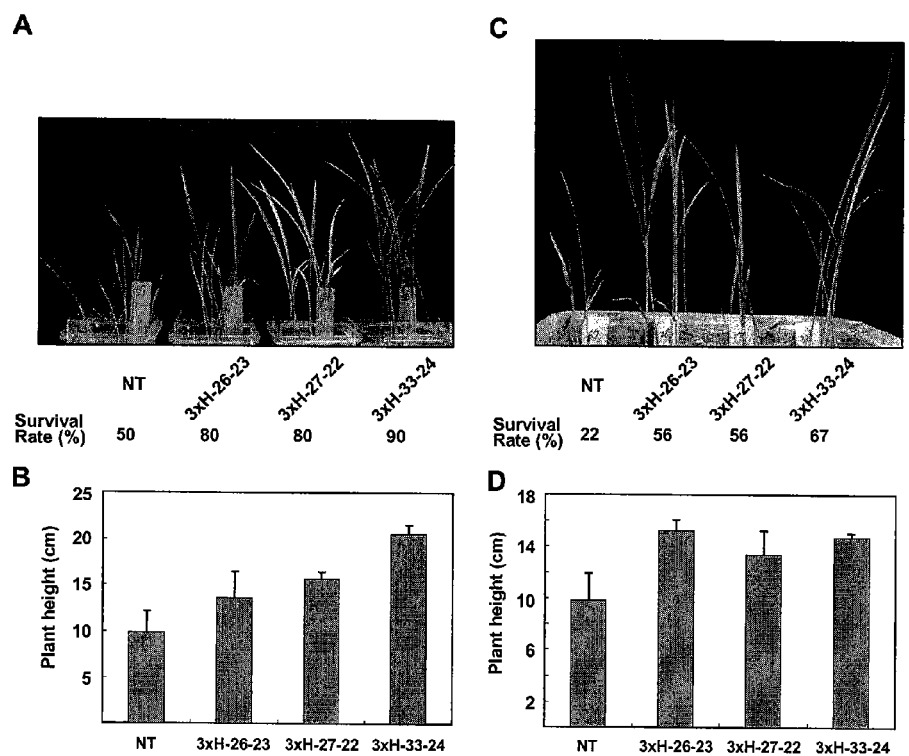
FIG. 9. illustrates that overexpression of HVA1 enhances salt tolerance of transgenic rice plants: (A) morphology and survival rates of plants germinated in 100 mM NaCl for 5 days and transferred to water for 14 days; (B) heights of plants germinated in 100 mM NaCl for 5 days and transferred to water for 14 days; (C) morphology and survival rates of plants germinated in 200 mM NaCl for 5 days and transferred to water for 14 days; (B) heights of plants germinated in 200 mM NaCl for 5 days and transferred to water for 14 days; wherein error bars indicate standard error of heights of ten seedlings.

With 100 mM NaCl, the survival rate was 50% for NT and was about 80-90% for the three transgenic lines (FIG. 9A), and the average plant heights were 10 cm for NT and 13.5, 15.5 and 20 cm for three transgenic lines (FIG. 9B). With 200 mM NaCl, the survival rate was 22% for NT and was about 56-67% for three transgenic lines (FIG. 9C), and the average plant heights were 10 cm for NT and 13.5-14.5 cm for three transgenic lines (FIG. 9D).

Overexpression of HVA1 Enhances Cold Tolerance of Transgenic Rice.

Figure 10:
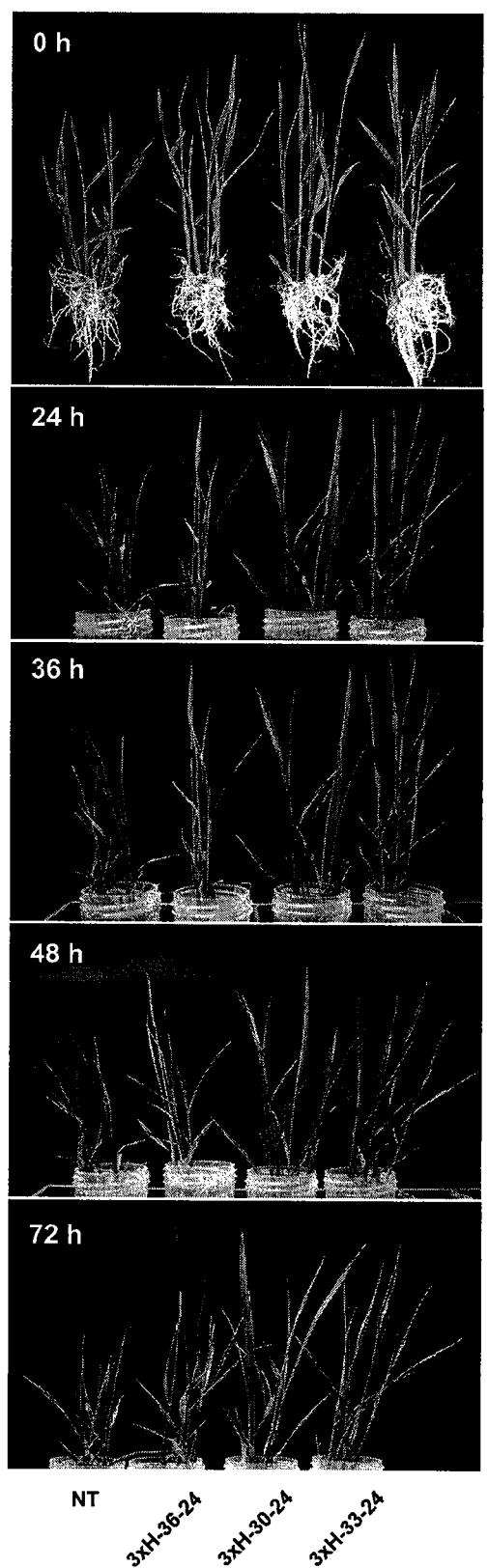
FIG. 10 are images of plants after the plants were transferred to 4° C. incubator for 0, 24, 36, 48 and 72 h.

Experiments were also performed to determine whether overexpression of HVA1 confers cold tolerance of transgenic rice. T2 seedlings of transgenic lines used for dehydration experiments described above were grown in hydroponic solution in 28° C. incubator for two weeks, then were transferred to a 4° C. incubator with 12 hour daily light for 0, 24, 36, 48 and 72 hours. Leaves of NT plants severely rolled up after 24 hours in cold, and growth of NT plants was hampered significantly thereafter (FIG. 10). Some leaves (mainly lower leaves) of transgenic lines also rolled up, but growth of the transgenic plants continued (FIG. 10).

Discussion

ABRC321 Confers High level ABA Induction and Transcription Strengths in Transgenic Rice Previous studies, by barley aleurone transient expression assays, have shown that HVA22 ABRC1 or HVA1 ABRC3 was sufficient for conferring ABA induction when fused to the Amy64 minimal promoter, and exchange and recombination of components of two ABRCs resulted in different promoter strength for transcription and ABA response (Shen et al., 1996). Although the combination of CE3 from ABRC3 with A3 and CE1 from ABRC1 conferred strongest ABA-inducible promoter activity, it also leads to high basal promoter activity in the absence of ABA; whereas, the combination of CE3 and A2 from ABRC3 with CE1 from ABRC1 conferred high ABA-induced promoter activity as well as low basal promoter activity in the absence of ABA (Shen et al., 1996). In order to minimize the basal promoter activity in the absence of ABA and stresses, and to maximize the ABA- or stress-induced promoter activity, ABRC321 combining CE3, A2 and CE1 was constructed and tested for its effectiveness in directing transgene expression in the present invention.

First by using GUS as the reporter in barley aleurone transient expression assays, it was shown that ABRC321 significantly enhanced the Amy64 minimal promoter activity in response to ABA, and the induction was proportional to the copy number of ABRC321 (FIG. 2). Four copies of the ABRC1, which confers ABA and dehydration induced activity to the rice Act1 minimal promoter (Su et al., 1998), has been used for expression of trehalose in transgenic rice for enhancement of tolerance to salt, drought and low temperature stresses (Garg et al., 2002). In the present invention, it was shown that although the absolute level of ABA induction with 1 copy of ABRC321 was similar to that with 1 copy of ABRC1, due to the lower basal promoter activity of ABRC321 in the absence of ABA, the magnitude of ABA induction with 1 copy of ABRC321 was 5 times of that with 1 copy of ABRC1 (FIG. 2).

The studies of the present invention indicate that ABRC321 conferred tighter control of ABA, and thus stress-induced gene expression than ABRC 1. Studies according to the present invention, by stable transgene expression assays, also demonstrated that 1-3 copies of ABRC321 conferred higher magnitude of ABA induction and absolute levels of ABA-induced promoter activity in leaves of transgenic rice as compared with the Amy 64 minimal promoter lacking ABRC321 (FIG. 3 A). The enhancement was even more significant with 3 copies of ABRC321 than with 1-2 copies of ABRC321 in roots of transgenic rice. Expression of HVA1 under the control of 3×ABRC321 has indeed led to low-level accumulation of HVA1 in vegetative tissues of many transgenic rice lines in the absence of ABA and high-level accumulation induced by ABA and various stresses. These studies demonstrated the advantage of using 3 copies of ABRC321 in designing promoters for ABA and stress-resistant gene expression.

ABRC321 is Under Developmental, Spatial and Stress Regulation in Transgenic Rice It is interesting to note that the barley derived ABRC321 is subjected to multiple regulations in transgenic rice as in barley. Previous GUS activity staining assay indicated that the Amy64 minimal promoter was active in the scutellum, while ABRC321 was highly active in the embryo and aleurone tissue of transgenic rice (FIG. 4). Accumulation of HVA1 under the control of ABRC321 was detected in seeds during mid- to late-stage of development (seeds mature at 25 days after anthesis in this experiment) (FIGS. 6A and 6B), but not in leaves and roots of transgenic seedlings (FIG. 5), under normal growth conditions. These studies indicate that ABRC321 is developmentally and spatially regulated in transgenic rice. Since ABRC321 directed HVA1 accumulation was up-regulated by ABA and dehydration in vegetative tissues of transgenic seedlings (FIG. 5 and FIG. 7A), the activity of ABRC321 in embryos and aleurone tissues of developing seeds could be up-regulated by the rise in ABA concentration and decline of water content in these tissues during mid- to late-stages of seed development (Taiz and Zeiger, 2006). On the other hand, without wishing to be bound by any theory, the decline of HVA1 accumulation during seed germination (FIG. 6C) and rewatering of plants (FIG. 7B) when ABA concentrations decreased (Taiz and Zeiger, 2006) suggests that ABRC321 might become inactive during these processes.

The developmental, spatial and stress regulations of ABRC321 in transgenic rice seeds and vegetative tissues are similar to the regulation of HVA1 and HVA22 genes/promoters in barley seeds and vegetative tissues (Hong et al., 1992; Straub et al., 1994; Shen et al., 2001), indicating that the 56-bp ABRC321 contains most, if not all, information for the developmental, spatial and stress regulation by conserved mechanisms in barley and rice. A barley basic domain/Leu zipper (bZIP) transcription factor, HvABI5, has been shown to bind to ABRCs of HVA1 and HVA22 in vitro in a sequence-specific manner, as well as to transactivate these two ABRCs in vivo (Casaretto and Ho, 2003). Another transcription factor, HvVP1, is necessary and cooperates with HvABI5 for the ABA induced ABRC activity (Casaretto and Ho, 2003). A rice HvABI5 homolog, TRAB1, has been shown to bind to ABRE and interact with a rice HvVP1 homolog, OsVP1, to mediate ABA-induced transcription (Hobo et al., 1999). These studies further suggest conservation in regulation of ABRC in barley and rice.

Figure 11:
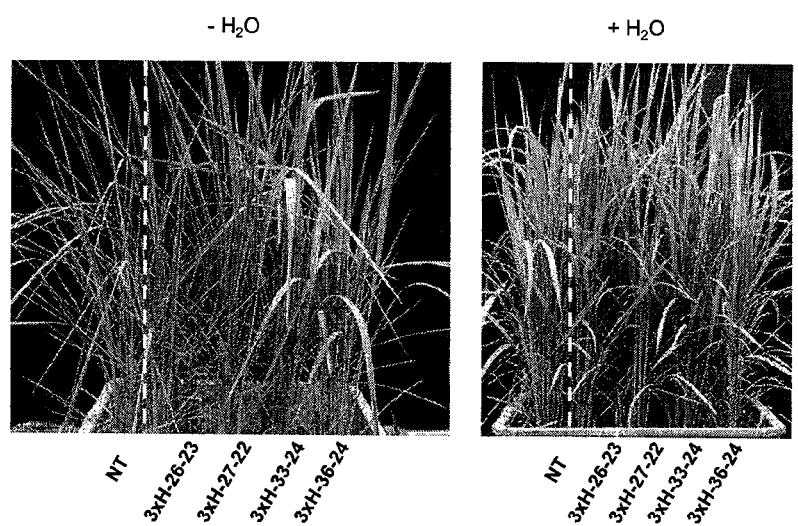
FIG. 11 are images of plants showing that T2 seedlings of transgenic rice lines carrying ABRC321-HVA1 grew normally under irrigation, and conferred higher strength of resistance to dehydration as compared to the non-transformant (NT): (A) plants were subjected to dehydration cycle (irrigated after soil was completely dried); (B) plants gown with irrigation.

ABRC321 is a Molecular Switch for Turning on Multiple Stress Tolerance of Transgenic Rice HVA1 has been expressed under the control of the constitutively active rice Act1 promoter in transgenic rice and oat, and under the control of the maize Ubi promoter in transgenic wheat. These transgenic plants showed improved tolerance to dehydration, osmotic and salt stresses (Xu et al., 1996; Sivamani et al., 2000; Maqbool et al., 2002). However, comparison of growth performance and productivity of transgenic plants with wild type plants under normal environmental conditions have not been extensively examined. In the present study, it was shown that the accumulation of HVA1 under the control of 3×ABRC321 was rather low in vegetative tissues, and plants grew as normal as or even with higher growth rate and strength than wild type plants under normal environmental conditions (FIG. 11). Accumulation of HVA1 was significantly enhanced by ABA and stresses in vegetative tissues of transgenic rice. These plants displayed significantly increased tolerance not only to dehydration and salt but also to cold that has not been reported previously in transgenic plants overexpressing HVA1, and exhibited more sustainable growth than wild type plants.

In summary, studies according to the present invention lead to the conclusion that ABRC321, preferably 3×ABRC321, could serve as a molecular switch for turning on expression of a stress-resistant gene, such as HVA1 to confer stress tolerance to the transgenic plant, such as the transgenic rice plant. This approach offers the following unique features: 1) the low background of HVA1 expression avoids unfavorable impact on rice plant growth and productivity under normal environmental conditions; 2) the endogenous HVA1 homologous protein is already present in the wild type rice seeds, therefore, the accumulation of the barley HVAL in transgenic rice seeds could be more desirable for public acceptance; 3) the accumulation of HVA1 in brown rice is restricted in embryos and aleurone layers, which could be removed as germ and bran during milling. Similar approaches could be applied to other plants for improvement of tolerance to a wide array of abiotic stresses without an apparent yield penalty.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

Bajaj S, Targolli J, Liu L F, Ho T D, Wu R (1999), Transgenic approaches to increase dehydration-stress tolerance in plants. Mol Breeding 5: 493-503.

Baker J, Steele C, Dure L I (1988), Sequence and characterizaiton of 6 LEA proteins and their genes from cotton. Plant Mol Biol 11: 277-291.

Bartels D (2001), Targeting detoxification pathways: an efficient approach to obtain plants with multiple stress tolerance? Trends Plant Sci 6: 284-286.

Boyer J (1982), Plant productivity and environment. Science 218: 443-448.

Bruce W B, Christensen A H, Klein T, Fromm M, Quail P H (1989), Photoregulation of a phytochrome gene promoter from oat transferred into rice by particle bombardment. Proc Natl Acad Sci USA 86: 9692-9696.

Casaretto J, Ho T H (2003), The transcription factors HvABI5 and HvVP1 are required for the abscisic acid induction of gene expression in barley aleurone cells. Plant Cell 15: 271-284.

Cercos M, Gomez-Cadenas A, Ho T H (1999), Hormonal regulation of a cysteine proteinase gene, EPB-1, in barley aleurone layers: cis- and trans-acting elements involved in the co-ordinated gene expression regulated by gibberellins and abscisic acid. Plant J 19:107-118.

Chandler P, Robertson M (1994), Gene expression regulated by abscisic acid and its relation to stress tolerance. Annu Rev Plant Physiol Plant Mol Biol 45: 113-141.

Chen P-W, Lu C-A, Yu T-S, Tseng T-H, Wang C—S, Yu S-M (2002), Rice alpha-amylase transcriptional enhancers direct multiple mode regulation of promoters in transgenic rice. J Biol Chem 277:13641-13649.

Dure L (1981) Developmental biochemistry of cotton seed embryogenesis and germinatoin: changing mRNA populations as shown in vitro and in vivo protein synthesis. Biochemistry 20: 4162-4168.

Dure L (1992) The LEA proteins of higher plants. In DPS Verma, ed., Control of Plant Gene Expression. CRC Press, Boca Raton, Fla., pp. 325-335.

Dure L, 3rd (1993) A repeating 11-mer amino acid motif and plant desiccation. Plant J 3: 363-369.

Dure L, Crouch M, Harada J, Ho T-H, Mundy J, Quantrano R, Thomas T, Sung Z (1989), Common amino acid sequence domains among the LEA proteins of higher plants. Plant Mol Biol 12: 475-486.

Fu D, Huang B, Xiao Y, Muthukrishnan S, Liang G (2007), Overexpression of barley hva gene in creeping bentgrass for improving drought tolerance. Plant Cell Rep (in press).

Garg A K, Kim J K, Owens T G, Ranwala A P, Choi Y D, Kochian L V, Wu R J (2002), Trehalose accumulation in rice plants confers high tolerance levels to different abiotic stresses. Proc Natl Acad Sci USA 99:15898-15903.

Goddijn O J, Verwoerd T C, Voogd E, Krutwagen R W, de Graaf P T, van Dun K, Poels J, Ponstein A S, Damm B, Pen J (1997) Inhibition of trehalase activity enhances trehalose accumulation in transgenic plants. Plant Physiol 113: 181-190.

Greenway H, Munns R (1980) Mechanisms of salt tolerance in nonhalophytes. Annu Rev Plant Physiol 31: 149-190.

Guiltinan M J, Marcotte W R, Jr., Quatrano R S (1990) A plant leucine zipper protein that recognizes an abscisic acid response element. Science 250: 267-271.

Himmelbach A, Yang Y, Grill E (2003) Relay and control of abscisic acid signaling. Curr Opin Plant Biol 6: 470-479.

Ho T-H D, Wu R (2004). Genetic engineering for enhancing plant productivity and stress tolerance. In H. T. Nguyen and A. Blum, ed., Physiology and Biotechology Integration for Plant Breeding. Marcel Dekker, Inc, New York, N.Y., pp. 489-502.

Hobo T, Kowyama Y, Hattori T (1999), A bZIP factor, TRAB1, interacts with VP1 and mediates abscisic acid-induced transcription. Proc Natl Acad Sci USA 96:15348-15353.

Hong B, Barg R, Ho T-H (1992), Developmental and organ-specific expression of an ABA- and stress-induced protein in barley. Plant Mol Biol 18: 663-674.

Hong B, Uknes S, Ho T-H (1988), Cloning and characterization of a cDNA enclding a mRNA rapidly induced by ABA in barley aleurone layers. Plant Mol Biol 11: 495-506.

Hsieh T H, Lee J T, Charng Y Y, Chan M T (2002), Tomato plants ectopically expressing *Arabidopsis* CBF1 show enhanced resistance to water deficit stress. Plant Physiol 130: 618-626.

Jefferson R, Kavanagh T, Bevan M W (1987), GUS fusion: beta-glucuronidase as a sensitive and versatile gene fusion marker in higher plants. EMBO J. 6: 3901-3907.

Kasuga M, Liu Q, Miura S, Yamaguchi-Shinozaki K, Shinozaki K (1999), Improving plant drought, salt, and freezing tolerance by gene transfer of a single stress-inducible transcription factor. Nat Biotechnol 17: 287-291.

Lanahan M B, Ho T H, Rogers S W, Rogers J C (1992), A gibberellin response complex in cereal alpha-amylase gene promoters. Plant Cell 4: 203-211

Lee J, Prasad V, Yang P, Wu J, Ho T-H, Chamg Y Y, Chan M T, (2003) Expression of *Arabidopsis* CBF1 regulated by an ABA/stress inducible promoter in transgenic tomato confers stress tolerance without affecting yield. Plant Cell Environ 26: 1181-1190.

Lu C-A, Lim E-K, Yu S-M (1998), Sugar response sequence in the promoter of a rice alpha-amylase gene serves as a transcriptional enhancer. J Biol Chem 273:10120-10131.

Maqbool S, Zhong H, E I-Maghraby Y, Ahmad A, Chai B, Wang W, Sabzikar R, Sticklen M (2002), Competence of oat (*Avena sativa* L.) shoot apical meristems for integrative transformation, inherited expression, and osmotic tolerance of transgenic lines containing hval. Theor Appl Genet. 105: 201-208.

Moons A, Bauw G, Prinsen E, Van Montagu M, Van der Straeten D (1995), Molecular and physiological responses to abscisic acid and salts in roots of salt-sensitive and salt-tolerant Indica rice varieties. Plant Physiol 107: 177-186.

Ried J L, Walker-Simmons M K (1993), Group 3 Late Embryogenesis Abundant Proteins in Desiccation-Tolerant Seedlings of Wheat (*Triticum aestivum* L.). Plant Physiol 102:125-131.

Romero C, Belles J, Vaya J, Serrano R, Culianez-Macia F (1997), Expression of the yeast trehalose-6-phosphate synthase gene in transgenic tobacco plants: pleiotropic phenotypes include drought tolerance. Planta 201: 293-297.

Shen Q, Chen C N, Brands A, Pan S M, Ho T H (2001), The stress- and abscisic acid-induced barley gene HVA22: developmental regulation and homologues in diverse organisms. Plant Mol Biol 45: 327-340.

Shen Q, Ho T H (1995), Functional dissection of an abscisic acid (ABA)-inducible gene reveals two independent ABA-responsive complexes each containing a G-box and a novel cis-acting element. Plant Cell 7: 295-307.

Shen Q, Uknes S J, Ho T H (1993), Hormone response complex in a novel abscisic acid and cycloheximide-inducible barley gene. J Biol Chem 268: 23652-23660.

Shen Q, Zhang P, Ho T H (1996), Modular nature of abscisic acid (ABA) response complexes: composite promoter units that are necessary and sufficient for ABA induction of gene expression in barley. Plant Cell 8:1107-1119.

Shen Q J, Casaretto J A, Zhang P, Ho T H (2004), Functional definition of ABA-response complexes: the promoter units necessary and sufficient for ABA induction of gene expression in barley (*Hordeum vulgare* L.). Plant Mol Biol 54: 111-124.

Shinozaki K, Yamaguchi-Shinozaki K, Seki M (2003), Regulatory network of gene expression in the drought and cold stress responses. Curr Opin Plant Biol 6: 410-417.

Sivamani E, Bahieldin A, Wraith J M, Al-Niemi T, Dyer W E, Ho T D, Qu R (2000), Improved biomass productivity and water use efficiency under water deficit conditions in transgenic wheat constitutively expressing the barley HVA1 gene. Plant Science 155:1-9.

Skriver K, Mundy J (1990) Gene expression in response to abscisic acid and osmotic stress. Plant Cell 2: 503-512.

Skriver K, Olsen F L, Rogers J C, Mundy J (1991) cis-acting DNA elements responsive to gibberellin and its antagonist abscisic acid. Proc Natl Acad Sci USA 88: 7266-7270.

Straub P F, Shen Q, Ho T D (1994) Structure and promoter analysis of an ABA- and stress-regulated barley gene, HVA1. Plant Mol Biol 26: 617-630.

Su J, Shen Q, David Ho T H, Wu R (1998) Dehydration-stress-regulated transgene expression in stably transformed rice plants. Plant Physiol 117: 913-922.

Sutton F, Ding X, Kenefick D G (1992), Group 3 LEA Gene HVA1 Regulation by Cold Acclimation and Deacclimation in Two Barley Cultivars with Varying Freeze Resistance. Plant Physiol 99: 338-340.

Taiz L, Zeiger E (2006), Abscisic acid: a seed maturation and antistress signal. Chapter 23, In: Plant Physiology, 4th edition. Sinauer Associates, Inc., pp. 594-613.

Xu D, Duan X, Wang B, Hong B, Ho T, Wu R (1996), Expression of a Late Embryogenesis Abundant Protein Gene, HVA1, from Barley Confers Tolerance to Water Deficit and Salt Stress in Transgenic Rice. Plant Physiol 110: 249-257.

Yamaguchi-Shinozaki K, Shinozaki K (2006) Transcriptional regulatory networks in cellular responses and tolerance to dehydration and cold stresses. Annu Rev Plant Biol 57: 781-803.

Yancey P H, Clark M E, Hand S C, Bowlus R D, Somero G N (1982) Living with water stress: evolution of osmolyte systems. Science 217:1214-1222.

Yu S-M, Kuo Y-H, Sheu G, Sheu Y-J, Liu L-F (1991). Metabolic derepression of alpha-amylase gene expression in suspension-cultured cells of rice. J Biol Chem 266: 21131-21137.

We claim:

1. A stably transformed transgenic monocot plant comprising a stress-responsive promoter operably linked to a coding region of a stress-resistant gene, wherein the stress-responsive promoter comprises at least two copies of a nucleotide sequence consisting of, from the 5'-end to the 3'-end of the promoter, in the order of:
   (a) the nucleotide sequence of SEQ ID NO: 1;
   (b) the nucleotide sequence of SEQ ID NO:2;
   (c) a nucleotide sequence consisting of 10 nucleotides; and
   (d) the nucleotide sequence of SEQ ID NO:3; wherein the stably transformed transgenic monocot plant consistently expresses the stress-resistant gene in response to abscisic acid (ABA) induction in a vegetative tissue and confers enhanced tolerance to one or more abiotic stresses as compared to a control plant of the same monocot plant species lacking said stress-responsive promoter.

2. The transgenic plant of claim 1 being a transgenic cereal plant.

3. A transgenic cereal grain produced from the transgenic cereal plant of claim 2.

4. The cereal grain of claim 3, being a rice grain.

5. The transgenic plant of claim 2, wherein the transgenic cereal plant is a stably transformed transgenic rice plant.

6. The transgenic plant of claim 5, wherein the stress-resistant gene is a HVA1 gene.

7. The transgenic plant of claim 1, wherein the stress-responsive promoter comprises at least two copies of SEQ ID NO: 4.

8. The transgenic plant of claim 1, wherein the stress-resistant gene encodes a protein selected from the group consisting of a stress-regulatory protein selected from a transcription factor, a protein kinase, an enzyme involved in phosphoinositide metabolism or an enzyme required for the synthesis of the plant hormone abscisic acid (ABA); a protein selected from an enzyme required for biosynthesis of an osmoprotectant or for a fatty acid metabolism; a chaperone; a proteinase inhibitor; a ferritin; a water channel protein; a sugar and proline transporter; a detoxification enzyme; a lipid-transfer protein; a transporter that maintains ionic homeostasis; an oxidative stress-related protein; an antifreeze protein (AFP) or ice structuring protein (ISP); a heat shock protein (HSP); a late embryogenesis abundant (LEA) protein; a protein involved in a stress-responsive metabolic pathway selected from amino acid metabolism, lipid metabolism or secondary metabolism; and a protein involved in photosynthesis.

9. The transgenic plant of claim 1, wherein the stress-resistant gene is selected from the group consisting of one or more trehalose biosynthetic genes, a transcription factor CBF1 gene, and a HVA1 gene.

10. The transgenic plant of claim 1, comprising the nucleotide sequence of SEQ ID NO:12, or SEQ ID NO:13.

* * * * *

SEQUENCE LISTING

```
<160> NUMBER OF SEQ ID NOS: 14

<210> SEQ ID NO 1
<211> LENGTH: 7
<212> TYPE: DNA
<213> ORGANISM: Hordeum vulgare

<400> SEQUENCE: 1 gcgtgtc                                                              7

<210> SEQ ID NO 2
<211> LENGTH: 7
<212> TYPE: DNA
<213> ORGANISM: Hordeum vulgare

<400> SEQUENCE: 2 acgtggc                                                              7

<210> SEQ ID NO 3
<211> LENGTH: 7
<212> TYPE: DNA
<213> ORGANISM: Hordeum vulgare

<400> SEQUENCE: 3 tgccacc                                                              7

<210> SEQ ID NO 4
<211> LENGTH: 41
<212> TYPE: DNA
<213> ORGANISM: artificial sequence
<220> FEATURE:
<223> OTHER INFORMATION: The sequence contains CE3 and ABRE2/A2 (A2)
      from HVA1 ABRC3 and CE1 from HVA22 ABRC1, and 10 bp artificial
      sequence between A2 and CE1.

<400> SEQUENCE: 4
acgcgtgtcc tccctacgtg gcggctcgag attgccaccg g                       41

<210> SEQ ID NO 5
<211> LENGTH: 56
<212> TYPE: DNA
<213> ORGANISM: artificial sequence
<220> FEATURE:
<223> OTHER INFORMATION: The sequence contains the ABRC321 sequence.

<400> SEQUENCE: 5
ggtaccgcaa cgcgtgtcct ccctacgtgg cggctcgaga ttgccaccgg tctaga        56

<210> SEQ ID NO 6
<211> LENGTH: 98
<212> TYPE: DNA
<213> ORGANISM: artificial sequence
<220> FEATURE:
<223> OTHER INFORMATION: The sequence contains the barley alpha-amylase
      gene minimal promoter (Amy64 mini P).
```

```
<400> SEQUENCE: 6
aattccggca tgccgcagca cactataaat acctggccag acacacaagc tgaatgcatc    60
agttctccat cgtactcttc gagagcacag caagagag                            98

<210> SEQ ID NO 7
<211> LENGTH: 166
<212> TYPE: DNA
<213> ORGANISM: artificial sequence
<220> FEATURE:
<223> OTHER INFORMATION: The sequence contains one copy (1x) of ABRC321
      and the Amy64 mini P.

<400> SEQUENCE: 7
ggtaccgcaa cgcgtgtcct ccctacgtgg cggctcgaga ttgccaccgg tctagagtcg    60
actgcagcaa ttccggcatg ccgcagcaca ctataaatac ctggccagac acacaagctg   120
aatgcatcag ttctccatcg tactcttcga gagcacagca agagag                  166

<210> SEQ ID NO 8
<211> LENGTH: 216
<212> TYPE: DNA
<213> ORGANISM: artificial sequence
<220> FEATURE:
<223> OTHER INFORMATION: The sequence contains two copies (2x) of
      ABRC321 and one copy of the Amy64 mini P.

<400> SEQUENCE: 8
ggtaccgcaa cgcgtgtcct ccctacgtgg cggctcgaga ttgccaccgg ggtaccgcaa    60
cgcgtgtcct ccctacgtgg cggctcgaga ttgccaccgg tctagagtcg actgcagcaa   120
ttccggcatg ccgcagcaca ctataaatac ctggccagac acacaagctg aatgcatcag   180
ttctccatcg tactcttcga gagcacagca agagag                             216

<210> SEQ ID NO 9
<211> LENGTH: 266
<212> TYPE: DNA
<213> ORGANISM: artificial sequence
<220> FEATURE:
<223> OTHER INFORMATION: The sequence contains three copies (3x) of
      ABRC321 and one copy of the Amy64 mini P.

<400> SEQUENCE: 9
ggtaccgcaa cgcgtgtcct ccctacgtgg cggctcgaga ttgccaccgg ggtaccgcaa    60
cgcgtgtcct ccctacgtgg cggctcgaga ttgccaccgg ggtaccgcaa cgcgtgtcct   120
ccctacgtgg cggctcgaga ttgccaccgg tctagagtcg actgcagcaa ttccggcatg   180
ccgcagcaca ctataaatac ctggccagac acacaagctg aatgcatcag ttctccatcg   240
tactcttcga gagcacagca agagag                                        266

<210> SEQ ID NO 10
<211> LENGTH: 213
<212> TYPE: PRT
<213> ORGANISM: Hordeum vulgare

<400> SEQUENCE: 10

Met Ala Ser Asn Gln Asn Gln Gly Ser Tyr His Ala Gly Glu Thr Lys
1               5                   10                  15

Ala Arg Thr Glu Glu Lys Thr Gly Gln Met Met Gly Ala Thr Lys Gln
            20                  25                  30

Lys Ala Gly Gln Thr Thr Glu Ala Thr Lys Gln Lys Ala Gly Glu Thr
        35                  40                  45
```

```
Ala Glu Ala Thr Lys Gln Lys Thr Gly Glu Thr Glu Ala Ala Lys
 50                  55                  60

Gln Lys Ala Ala Glu Ala Lys Asp Lys Thr Ala Gln Thr Ala Gln Ala
 65                  70                  75                  80

Ala Lys Asp Lys Thr Tyr Glu Thr Ala Gln Ala Ala Lys Glu Arg Ala
                 85                  90                  95

Ala Gln Gly Lys Asp Gln Thr Gly Ser Ala Leu Gly Glu Lys Thr Glu
                100                 105                 110

Ala Ala Lys Gln Lys Ala Ala Glu Thr Thr Glu Ala Ala Lys Gln Lys
            115                 120                 125

Ala Ala Glu Ala Thr Glu Ala Ala Lys Gln Lys Ala Ser Asp Thr Ala
        130                 135                 140

Gln Tyr Thr Lys Glu Ser Ala Val Ala Gly Lys Asp Lys Thr Gly Ser
145                 150                 155                 160

Val Leu Gln Gln Ala Gly Glu Thr Val Val Asn Ala Val Val Gly Ala
                165                 170                 175

Lys Asp Ala Val Ala Asn Thr Leu Gly Met Gly Gly Asp Asn Thr Ser
            180                 185                 190

Ala Thr Lys Asp Ala Thr Thr Gly Ala Thr Val Lys Asp Thr Thr Thr
        195                 200                 205

Thr Thr Arg Asn His
    210
```

<210> SEQ ID NO 11
<211> LENGTH: 840
<212> TYPE: DNA
<213> ORGANISM: artificial sequence
<220> FEATURE:
<223> OTHER INFORMATION: The sequence contains 1x ABRC321, the Amy64 mini P, and the coding sequence of the barley HVA22 protein.

<400> SEQUENCE: 11

```
ggtaccgcaa cgcgtgtcct ccctacgtgg cggctcgaga ttgccaccgg tctagagtcg    60
actgcagcaa ttccggcatg ccgcagcaca ctataaatac ctggccagac acacaagctg   120
aatgcatcag ttctccatcg tactcttcga gagcacagca agagagtgat catttcaggt   180
aagatcctag agtcgaccat ggcctccaac cagaaccagg ggagctacca cgccggcgag   240
accaaggccc gcaccgagga gaagaccggg cagatgatgg cgccaccaa gcagaaggcg    300 gggcagacca ccgaggccac caagcagaag gccggcgaga cggccgaggc caccaagcag   360
aagaccggcg agacggccga ggccgccaag cagaaggccg ccgaggccaa ggacaagacg   420
gcgcagacgg cgcaggcggc caaggacaag acgtacgaga cggcgcaggc ggccaaggag   480
cgcgccgccc agggcaagga ccagaccggc agcgccctcg gcgagaagac ggaggcggcc   540
aagcagaagg ccgccgagac gacggaggcg gccaagcaga aggccgccga ggcaaccgag   600
gcggccaagc agaaggcgtc cgacacggcg cagtacacca aggagtccgc ggtggccggc   660
aaggacaaga ccggcagcgt cctccagcag gccggcgaga cggtggtgaa cgccgtggtg   720
ggcgccaagg acgccgtggc aaacacgctg ggcatgggag gggacaacac cagcgccacc   780
aaggacgcca ccaccggcgc caccgtcaag gacaccacca ccaccaccag gaatcactag   840
```

<210> SEQ ID NO 12
<211> LENGTH: 890
<212> TYPE: DNA
<213> ORGANISM: artificial sequence

```
<220> FEATURE:
<223> OTHER INFORMATION: The sequence contains 2x ABRC321, the Amy64
      mini P, and the coding sequence of the barley HVA22 protein.

<400> SEQUENCE: 12
ggtaccgcaa cgcgtgtcct ccctacgtgg cggctcgaga ttgccaccgg ggtaccgcaa      60
cgcgtgtcct ccctacgtgg cggctcgaga ttgccaccgg tctagagtcg actgcagcaa     120
ttccggcatg ccgcagcaca ctataaatac ctggccagac acacaagctg aatgcatcag     180
ttctccatcg tactcttcga gagcacagca agagagtgat catttcaggt aagatcctag     240
agtcgaccat ggcctccaac cagaaccagg ggagctacca cgccggcgag accaaggccc     300
gcaccgagga gaagaccggg cagatgatgg gcgccaccaa gcagaaggcg gggcagacca     360
ccgaggccac caagcagaag gccggcgaga cggccgaggc caccaagcag aagaccggcg     420
agacggccga ggccgccaag cagaaggccg ccgaggccaa ggacaagacg gcgcagacgg     480
cgcaggcggc caaggacaag acgtacgaga cggcgcaggc ggccaaggag cgcgccgccc     540
agggcaagga ccagaccggc agcgccctcg gcgagaagac ggaggcggcc aagcagaagg     600
ccgccgagac gacggaggcg gccaagcaga aggccgccga ggcaaccgag gcggccaagc     660
agaaggcgtc cgacacggcg cagtacacca aggagtccgc ggtggccggc aaggacaaga     720
ccggcagcgt cctccagcag gccggcgaga cggtggtgaa cgccgtggtg ggcgccaagg     780
acgccgtggc aaacacgctg ggcatgggag gggacaacac cagcgccacc aaggacgcca     840
ccaccggcgc caccgtcaag gacaccacca ccaccaccag gaatcactag                 890

<210> SEQ ID NO 13
<211> LENGTH: 940
<212> TYPE: DNA
<213> ORGANISM: artificial sequence
<220> FEATURE:
<223> OTHER INFORMATION: The sequence contains 3x ABRC321, the Amy64
      mini P, and the coding sequence of the barley HVA22 protein.

<400> SEQUENCE: 13
ggtaccgcaa cgcgtgtcct ccctacgtgg cggctcgaga ttgccaccgg ggtaccgcaa      60
cgcgtgtcct ccctacgtgg cggctcgaga ttgccaccgg ggtaccgcaa cgcgtgtcct     120
ccctacgtgg cggctcgaga ttgccaccgg tctagagtcg actgcagcaa ttccggcatg     180
ccgcagcaca ctataaatac ctggccagac acacaagctg aatgcatcag ttctccatcg     240
tactcttcga gagcacagca agagagtgat catttcaggt aagatcctag agtcgaccat     300
ggcctccaac cagaaccagg ggagctacca cgccggcgag accaaggccc gcaccgagga     360
gaagaccggg cagatgatgg gcgccaccaa gcagaaggcg gggcagacca ccgaggccac     420
caagcagaag gccggcgaga cggccgaggc caccaagcag aagaccggcg agacggccga     480
ggccgccaag cagaaggccg ccgaggccaa ggacaagacg gcgcagacgg cgcaggcggc     540
caaggacaag acgtacgaga cggcgcaggc ggccaaggag cgcgccgccc agggcaagga     600
ccagaccggc agcgccctcg gcgagaagac ggaggcggcc aagcagaagg ccgccgagac     660
gacggaggcg gccaagcaga aggccgccga ggcaaccgag gcggccaagc agaaggcgtc     720
cgacacggcg cagtacacca aggagtccgc ggtggccggc aaggacaaga ccggcagcgt     780
cctccagcag gccggcgaga cggtggtgaa cgccgtggtg ggcgccaagg acgccgtggc     840
aaacacgctg ggcatgggag gggacaacac cagcgccacc aaggacgcca ccaccggcgc     900
caccgtcaag gacaccacca ccaccaccag gaatcactag                            940
```

```
<210> SEQ ID NO 14
<211> LENGTH: 56
<212> TYPE: DNA
<213> ORGANISM: artificial sequence
<220> FEATURE:
<223> OTHER INFORMATION: complement of SEQ ID NO:5

<400> SEQUENCE: 14
tctagaccgg tggcaatctc gagccgccac gtagggagga cacgcgttgc ggtacc      56
```